US012427322B2

(12) United States Patent
Lee et al.

(10) Patent No.: US 12,427,322 B2
(45) Date of Patent: Sep. 30, 2025

(54) DEVICES, SYSTEMS AND METHODS FOR IMPROVING CONDUCTIVE COMMUNICATION BETWEEN EXTERNAL DEVICES AND IMPLANTABLE MEDICAL DEVICES

(71) Applicant: Pacesetter, Inc., Sylmar, CA (US)

(72) Inventors: Frank Lee, San Leandro, CA (US); Thanh Tieu, Simi Valley, CA (US); Robert Williams, San Jose, CA (US); Suyashree Bhonsle, Menlo Park, CA (US); Jinto Zacharias, Los Angeles, CA (US); Matthew G. Fishler, Scotts Valley, CA (US); Suresh Gurunathan, Palo Alto, CA (US); Benjamin T. Persson, Saratoga, CA (US)

(73) Assignee: Pacesetter, Inc., Sylmar, CA (US)

( * ) Notice: Subject to any disclaimer, the term of this patent is extended or adjusted under 35 U.S.C. 154(b) by 689 days.

(21) Appl. No.: 17/701,132

(22) Filed: Mar. 22, 2022

(65) Prior Publication Data

US 2022/0212019 A1 Jul. 7, 2022

Related U.S. Application Data

(63) Continuation-in-part of application No. 17/222,279, filed on Apr. 5, 2021, now Pat. No. 11,925,811, and
(Continued)

(51) Int. Cl.
*A61N 1/372* (2006.01)
*A61B 5/00* (2006.01)
(Continued)

(52) U.S. Cl.
CPC ........ *A61N 1/37217* (2013.01); *A61B 5/0028* (2013.01); *A61B 5/0031* (2013.01);
(Continued)

(58) Field of Classification Search
CPC ............ A61N 1/37217; A61N 1/37211; A61N 1/37288; A61B 5/0028; H04B 13/005
See application file for complete search history.

(56) References Cited

U.S. PATENT DOCUMENTS 8,942,818 B2 * 1/2015 Markowitz .......... A61B 5/0028
607/30
9,168,383 B2 10/2015 Jacobson et al.
(Continued)

OTHER PUBLICATIONS

Response to Office Action dated Aug. 7, 2023, U.S. Appl. No. 17/222,242, filed Apr. 5, 2021.
(Continued)

*Primary Examiner* — George R Evanisko
(74) *Attorney, Agent, or Firm* — Pearl Cohen Zedek Latzer Baratz LLP

(57) ABSTRACT

Described herein are external devices, and methods for use therewith, that are configured to communicate with one or more implantable medical devices (IMDs) implanted within a patient using conductive communication, wherein the external device includes or is communicatively coupled to at least three external electrodes that are in contact with the patient. Certain such methods involve the external device identifying, for each IMD, of the plurality of IMDs, which one of the plurality of communication vectors is a preferred communication vector for communicating with the IMD, based on respective indicators of conductive communication quality that are determined for the plurality of communication vectors. Certain embodiments involve determining when there should be a reassessment of which one of the plurality of communication vectors is the preferred communication vector for communicating with an IMD, and in response thereto, identifying an updated preferred communication vector for communicating with the IMD.

20 Claims, 12 Drawing Sheets

Related U.S. Application Data a continuation-in-part of application No. 17/222,242, filed on Apr. 5, 2021, now Pat. No. 11,918,817.

(60) Provisional application No. 63/033,737, filed on Jun. 2, 2020, provisional application No. 63/005,628, filed on Apr. 6, 2020.

(51) Int. Cl.
  *A61N 1/362* (2006.01)
  *A61N 1/375* (2006.01)
  *A61N 1/39* (2006.01)

(52) U.S. Cl.
  CPC ............ *A61B 5/6869* (2013.01); *A61N 1/362* (2013.01); *A61N 1/3756* (2013.01); *A61N 1/3956* (2013.01)

(56) References Cited

U.S. PATENT DOCUMENTS

| | | | |
|---|---|---|---|
| 9,592,393 | B2 | 3/2017 | Stahmann et al. |
| 9,867,990 | B2 * | 1/2018 | Cinbis ............... A61B 5/0028 |
| 10,213,610 | B2 | 2/2019 | Maile et al. |
| 10,722,720 | B2 * | 7/2020 | Stahmann .......... A61N 1/37288 |
| 10,946,202 | B2 | 3/2021 | Maile et al. |
| 2011/0301435 | A1 | 12/2011 | Albert et al. |
| 2014/0221859 | A1 | 8/2014 | Albert |
| 2015/0174414 | A1 | 6/2015 | Stahmann et al. |
| 2015/0196769 | A1 | 7/2015 | Stahmann et al. |
| 2016/0059007 | A1 | 3/2016 | Koop |
| 2016/0271406 | A1 | 9/2016 | Maile et al. |
| 2018/0021583 | A1 | 1/2018 | Ciciarelli et al. |
| 2018/0078777 | A1 | 3/2018 | Wu et al. |
| 2018/0140853 | A1 | 5/2018 | Maile et al. |
| 2018/0178022 | A1 | 6/2018 | Koop et al. |
| 2018/0200525 | A1 | 7/2018 | Schilling et al. |
| 2018/0207433 | A1 | 7/2018 | Koop et al. |
| 2019/0201701 | A1 | 7/2019 | Balczewski et al. |
| 2022/0212019 | A1 | 7/2022 | Lee et al. |
| 2024/0165414 | A1 | 5/2024 | Fishler et al. |

OTHER PUBLICATIONS

Notice of Allowance dated Oct. 12, 2023, U.S. Appl. No. 17/222,242, filed Apr. 5, 2021.
Non-final Office Action dated May 23, 2023, U.S. Appl. No. 17/222,279.
Non-final Office Action dated Jun. 21, 2023, U.S. Appl. No. 17/222,242, filed Apr. 5, 2021.
Response to Office Action dated Aug. 1, 2023, U.S. Appl. No. 17/222,279.
Notice of Allowance dated Nov. 8, 2023, U.S. Appl. No. 17/222,279, filed Apr. 5, 2021.
Restriction Requirement dated Dec. 29, 2022, U.S. Appl. No. 17/222,279, filed Apr. 5, 2021.
Response to Restriction Requirement dated Feb. 10, 2023, U.S. Appl. No. 17/222,279, filed Apr. 5, 2021.
Restriction Requirement dated Apr. 10, 2023, U.S. Appl. No. 17/222,242, filed Apr. 5, 2021.
Response to Restriction dated Apr. 13, 2023, U.S. Appl. No. 17/222,242, filed Apr. 5, 2021.

* cited by examiner

DEVICES, SYSTEMS AND METHODS FOR IMPROVING CONDUCTIVE COMMUNICATION BETWEEN EXTERNAL DEVICES AND IMPLANTABLE MEDICAL DEVICES

PRIORITY

This application claims priority to U.S. Provisional Patent Application No. 63/291,772, titled DEVICES, SYSTEMS AND METHODS FOR IMPROVING CONDUCTIVE COMMUNICATION BETWEEN EXTERNAL DEVICES AND IMPLANTABLE MEDICAL DEVICES filed Dec. 20, 2021. Additionally, this application is a continuation-in-part (CIP) of U.S. patent application Ser. No. 17/222,242, titled "REMOTE FOLLOW-UP METHODS, SYSTEMS, AND DEVICES FOR LEADLESS PACEMAKER SYSTEMS" filed Apr. 5, 2021 (13881USO1_SJUD-01173US2), which claims priority to U.S. Provisional Patent Application No. 63/005,628, filed Apr. 6, 2020, and U.S. Provisional Patent Application No. 63/033,737, filed Jun. 2, 2020. This application is also continuation-in-part (CIP) of U.S. patent application Ser. No. 17/222,279, titled "REMOTE FOLLOW-UP METHODS, SYSTEMS, AND DEVICES FOR LEADLESS PACEMAKER SYSTEMS" filed Apr. 5, 2021 (13881USO2_SJUD-01173US3), which claims priority to U.S. Provisional Patent Application No. 63/005,628, filed Apr. 6, 2020, and U.S. Provisional Patent Application No. 63/033,737, filed Jun. 2, 2020. Priority is claimed to each of the above applications, and each of the above applications is incorporated herein by reference.

FIELD OF TECHNOLOGY

Embodiments described herein generally relate to devices, systems and methods that enable an external device, such as an external programmer or a remote monitor, to perform conductive communication with one or more implantable medical devices implanted within a patient using external electrodes that are in contact with the patient.

BACKGROUND

From time to time a non-implanted device needs to communicate with an implantable medical device (IMD), such as a leadless pacemaker (LP), so that the non-implanted device can, for example, program the IMD, interrogate the IMD, and/or obtain notifications and/or other types of diagnostic information from the IMD. Such a non-implanted device, which can also be referred to as an external device, can be, e.g., an external programmer or a remote monitor.

Communication between an external device and one or more IMDs (e.g., LPs) may be facilitated by conductive communication via patient tissue, whereby two skin electrodes (that are part of or coupled to the external device) are attached to skin of a patient within which (i.e., in whom) one or more IMDs is/are implanted, and the two skin electrodes are used to transmit information to and/or receive information from the IMD(s) via conduction through body tissue of the patient. In other words, the two skin electrodes can be used by the external device to transmit conductive communication signals via patient tissue to individual IMDs. Additionally, or alternatively, the two skin electrodes can be used by the external device to receive conductive communication signals from individual IMDs. The communication signals transmitted from an external device to an IMD, or vice versa, to achieve conductive communication can be referred to herein as conductive communication signals. The skin electrodes are examples of external electrodes, i.e., non-implanted electrodes.

Where conductive communication signals are transmitted from an external programmer to an IMD, the conductive communication signals can also be referred to more specifically as conductive programmer-to-implant (p2i) communication signals, or more succinctly as conductive p2i signals. Where the conductive communication signals are transmitted from an IMD to an external programmer, the conductive communication signals can also be referred to more specifically as conductive implant-to-programmer (i2p) communication signals, or more succinctly as conductive i2p signals. Conductive communication signals are also referred to sometimes as conducted communication signals, and these terms are often used interchangeably.

One potential problem with using conductive communication signals is that the orientation of the IMD(s) can cause fading that can adversely affect both conductive p2i and i2p communication. Additionally, the locations of the two skin electrodes, which define a communication vector for the external device, may not provide for good communication signal quality between the external device and an IMD. More generally, the orientation and location of an IMD and the locations of the external electrodes can affect the communication quality between an external device and an IMD. These problems may be exacerbated when there is a need or desire for the external device to communicate with multiple (i.e., two or more) IMDs. For example, it may be the case that a communication vector associated with two skin electrodes attached to a patient's skin provides for good conductive communication signal quality with only one of multiple IMDs. To overcome this problem, the two skin electrodes attached to the patient's skin at first locations can first be used to provide for conductive communication between the external device and a first IMD. The two skin electrodes can then be moved to second locations and then used to provide for conductive communication between the external device and a second IMD. If the patient also includes a third IMD, the two skin electrodes can then be moved to third locations and then used to provide for conductive communication between the external device and the third IMD. Even if a patient only includes a single IMD, it still may be necessary to move one or both of the two skin electrodes one or more times before acceptable conductive communication signal quality is achieved between the external device and the single IMD. This repositioning or moving of the two skin electrodes can be time consuming for both the patient and the medical personnel, as well as costly in terms of increasing the patient's medical bills.

SUMMARY

Certain embodiments of the present technology are related to methods for use by an external device that is configured to communicate with an IMD implanted within a patient using conductive communication, wherein the external device includes or is communicatively coupled to at least three external electrodes that are in contact with the patient. The external device can be, for example, an external programmer or a remote monitor, but is not limited thereto. The IMD can be, e.g., a leadless cardiac pacemaker, an insertable cardiac monitor (ICM), or a non-vascular implantable cardioverter defibrillator (NV-ICD), but is not limited thereto. Such a method can include determining a respective indicator of conductive communication quality for each communication vector, of a plurality of communication vectors that can be used to communicate with the IMD, wherein each of the plurality of communication vectors comprises a different combination (e.g., pair) of the at least three external electrodes that are in contact with the patient. Unless stated otherwise, when an external electrode is in contact with a patient it is presumed that the electrode is directly in contact with skin of the patient. The method can also include identifying which one of the plurality of communication vectors is a preferred communication vector for communicating with the IMD, based on the respective indicators of conductive communication quality that are determined for the plurality of communication vectors, and communicating with the IMD using the preferred communication vector for communicating with the IMD, after the preferred communication vector is identified.

In accordance with certain embodiments, the method can include, while or after communicating with the IMD using the preferred communication vector for communicating with the IMD, determining whether there should be a reassessment of which one of the plurality of communication vectors is the preferred communication vector for communicating with the IMD. The method can also include, in response to determining that there should be the reassessment, repeating the determining and the identifying steps, which may result in a new preferred communication vector being identified. The determining that there should be the reassessment can occur in response to the indicator of conductive communication quality associated with the preferred communication vector for communicating with the IMD falling below a corresponding threshold, in response to a loss of conductive communication with the IMD, or in response to a specified period of time elapsing since the preferred communication vector for communicating with the IMD was most recently identified.

In accordance with certain embodiments, a plurality of IMDs that are configured to perform conductive communication are implanted within the patient, and the external device is configured to communicate with each of the plurality of IMDs using conductive communication. In certain such embodiments, the determining, the identifying, and the communicating steps are each separately performed for each of the plurality of IMDs, such that a respective preferred communication vector is separately identified for each of the plurality of IMDs that are configured to perform conductive communication. This can result in a different preferred communication vector being identified for each of the IMDs. Alternatively, it is possible that the same preferred communication vector can be identified for two or more of the IMDs.

In accordance with certain embodiments, instructions can be provided to a user of the external device to modify at least one of where or how one or more of the at least three external electrodes contact the patient, in response to determining that the indicators of conductive communication quality for communicating with the IMD, which are determined for the plurality of communication vectors, are below a corresponding threshold. Such instructions can be provided via a display of the external device, and/or may be auditory type instructions. Other variations are also possible.

In accordance with certain embodiments, determining the respective indicator of conductive communication quality for each communication vector, of the plurality of communication vectors that can be used to communicate with the IMD, includes for each communication vector: determining a plurality of different measures of conductive communication quality and/or surrogates thereof for the communication vector; and combining the plurality of different measures of conductive communication quality and/or surrogates thereof to produce the respective indicator of conductive communication quality for the communication vector.

In accordance with certain embodiments, the plurality of different measures of conductive communication signal quality and/or the surrogates thereof that are determined for each communication vector, of the plurality of communication vectors that can be used to communicate with the IMD, are indicative of at least two of the following: a noise floor associated with the communication vector; a measure of amplitude of at least a portion of a conductive communication signal received by the external device from the IMD using the communication vector; a measure of amplitude of at least a portion of a conductive communication signal received by the IMD from the external device; a magnitude of at least a portion of a conductive communication signal received by the external device from the IMD after rectification and integration thereof; a magnitude of at least a portion of a conductive communication signal received by the IMD from the external device after rectification and integration thereof; a signal-to-noise ratio (SNR) of at least a portion of a conductive communication signal received by the external device from the IMD; a SNR of at least a portion of a conductive communication signal received by the IMD from the external device; a total energy of at least a portion of a conductive communication signal received by the external device from the IMD, after rectification and integration thereof; a total energy of at least a portion of a conductive communication signal received by the IMD from the external device, after rectification and integration thereof; a bit-error-rate (BER) associated with at least a portion of a conductive communication signal received by the external device from the IMD; and a BER associated with at least a portion of a conductive communication signal received by the IMD from the external device. The use of additional and/or alternative measures of conductive communication signal quality and/or the surrogates thereof is also possible and within the scope of the embodiments described herein.

In accordance with certain embodiments, identifying which one of the plurality of communication vectors is the preferred communication vector for communicating with the IMD, comprises ranking the plurality of communication vectors, and identifying a highest ranked one of the plurality of communication vectors as the preferred communication vector for communicating with the IMD.

In accordance with certain embodiments, identifying which one of the plurality of communication vectors is the preferred communication vector for communicating with the IMD, comprises identifying which one of the plurality of communication vectors has a highest indicator of conductive communication quality.

In accordance with certain embodiments, a plurality of IMDs that are configured to perform conductive communication are implanted within the patient, and the external device is configured to communicate with each of the plurality of IMDs using conductive communication. In certain such embodiments, the determining step is separately performed for each of the plurality of IMDs, such that for each of the IMDs a respective indicator of conductive communication quality is determined for each communication vector, of the plurality of communication vectors that can be used to communicate with the IMD, and the identifying step is performed collectively for the plurality of IMDs to thereby identify one preferred communication vector for communicating with the plurality of IMDs. Communicating with the plurality of IMDs is then performed using the one preferred communication vector for communicating with the IMD, after the one preferred communication vector is identified.

Certain embodiments of the present technology are related to an external device that is configured to communicate with an IMD implanted within a patient using conductive communication, wherein the external device comprises a conductive communication receiver, switches, and a controller, with the switches being between the conductive communication receiver and at least three external electrodes that are configured to be placed in contact with the patient. In accordance with certain embodiments, the controller of the external device is configured to control the switches to thereby control which communication vector, of a plurality of communication vectors that can be used to communicate with the IMD, is coupled to the conductive communication receiver, wherein each of the plurality of communication vectors comprises a different combination (e.g., pair) of the at least three external electrodes. The controller is also configured to determine a respective indicator of conductive communication quality for each communication vector, of the plurality of communication vectors that can be used to communicate with the IMD. Additionally, the controller is configured to identify which one of the plurality of communication vectors is a preferred communication vector for communicating with the IMD, based on the respective indicators of conductive communication quality that are determined for the plurality of communication vectors, and use the preferred communication vector to communicate with the IMD, after the preferred communication vector is identified.

In accordance with certain embodiments, the controller of the external device is also configured to determine when there should be a reassessment of which one of the plurality of communication vectors is the preferred communication vector for communicating with the IMD. In certain such embodiments, the controller is configured to determine that there should be the reassessment in response to at least one of the following: the indicator of conductive communication quality associated with the preferred communication vector for communicating with the IMD falling below a corresponding threshold; a loss of conductive communication with the IMD; or a specified period of time elapsing since the preferred communication vector for communicating with the IMD was most recently identified. Other variations are also possible and within the scope of the embodiments described herein.

In accordance with certain embodiments, the external device is configured to communicate with each of a plurality of IMDs that are configured to perform conductive communication. In certain such embodiments, for each IMD of the plurality of IMDs that are configured to perform conductive communication, the controller of the external device is configured to: determine a respective indicator of conductive communication quality for each communication vector, of the plurality of communication vectors that can be used to communicate with the IMD; identify which one of the plurality of communication vectors is a preferred communication vector for communicating with the IMD, based on the respective indicators of conductive communication quality that are determined for the plurality of communication vectors; and use the preferred communication vector to communicate with the IMD, after the preferred communication vector is identified, such that different said preferred communication vectors can be identified and used for communicating with different ones of the plurality of IMDs.

In accordance with certain embodiments, in order to determine the respective indicator of conductive communication quality for each communication vector, of the plurality of communication vectors that can be used to communicate with the IMD, the controller is configured to determine, for each communication vector, a plurality of different measures of conductive communication quality and/or surrogates thereof for the communication vector, and combine the plurality of different measures of conductive communication quality and/or surrogates thereof to produce the respective indicator of conductive communication quality for the communication vector. Examples of the different measures of conductive communication signal quality and/or the surrogates thereof were provided above, and thus need not be repeated.

In accordance with certain embodiments, in order to identify which one of the plurality of communication vectors is the preferred communication vector for communicating with the IMD, the controller is configured to rank the plurality of communication vectors, and identify a highest ranked one of the plurality of communication vectors as the preferred communication vector for communicating with the IMD. In accordance with certain embodiments, in order to identify which one of the plurality of communication vectors is the preferred communication vector for communicating with the IMD, the controller is configured to identify which one of the plurality of communication vectors has a highest indicator of conductive communication quality, without necessarily performing any ranking.

In accordance with certain embodiments, the external device is configured to communicate with each of a plurality of IMDs that are configured to perform conductive communication. In certain such embodiments, for each IMD of the plurality of IMDs that are configured to perform conductive communication, the controller is configured to determine a respective indicator of conductive communication quality for each communication vector of the plurality of communication vectors that can be used to communicate with the IMD. Additionally, the controller is configured to collectively identify one preferred communication vector for communicating with the plurality of IMDs, based on the respective indicators of conductive communication quality that have been determined. The controller is further configured to use the one preferred communication vector to communicate with the plurality of IMDs, after the one preferred communication vector is identified.

Certain embodiments of the present technology are directed to a method for use by an external device that is configured to communicate with each IMD, of a plurality of IMDs implanted within a patient, using conductive communication, wherein the external device includes or is communicatively coupled to at least three external electrodes that are in contact with the patient. Certain such embodiments comprise, for each IMD, of the plurality of IMDs, determining a respective indicator of conductive communication quality for each communication vector, of a plurality of communication vectors that can be used to communicate with the IMD, wherein each of the plurality of communication vectors comprises a different combination (e.g., pair) of the at least three external electrodes that are in contact with the patient. Additionally, for each IMD, of the plurality of IMDs, the method comprises identifying which one of the plurality of communication vectors is a preferred communication vector for communicating with the IMD, based on the respective indicators of conductive communication quality that are determined for the plurality of communication vectors. The method also comprises for each IMD, of the plurality of IMDs, communicating with the IMD using the preferred communication vector for communicating with the IMD, after the preferred communication vector for communicating with the IMD is identified. Further, the method comprises, for a said IMD, of the plurality of IMDs, determining that there should be a reassessment of which one of the plurality of communication vectors is the preferred communication vector for communicating with the IMD, and in response thereto, repeating the determining and the identifying steps for the IMD to thereby identify an updated preferred communication vector for communicating with the IMD. In accordance with certain such embodiments, the determining that there should be a reassessment of which one of the plurality of communication vectors is the preferred communication vector for communicating with the IMD occurs in response to at least one of the following: the indicator of conductive communication quality associated with the preferred communication vector for communicating with the IMD falling below a corresponding threshold; or a loss of conductive communication with the IMD.

This summary is not intended to be a complete description of the embodiments of the present technology. Other features and advantages of the embodiments of the present technology will appear from the following description in which the preferred embodiments have been set forth in detail, in conjunction with the accompanying drawings and claims.

BRIEF DESCRIPTION OF THE DRAWINGS

Embodiments of the present technology relating to both structure and method of operation may best be understood by referring to the following description and accompanying drawings, in which similar reference characters denote similar elements throughout the several views.

DETAILED DESCRIPTION

Embodiments of the present technology can be used to improve conductive communication between an external device and one or more implantable medical devices (IMDs) in time and cost efficient manners. Certain such embodiments improve and preferably optimize the conductive communication signal quality between an external device and each IMD, of a plurality of IMDs, by dynamically switching between multiple electrode combinations (e.g., pairs) to find a preferred conductive communication vector. Certain embodiments described herein provide details of how the communication signal quality is assessed for a given communication vector, and the criteria used to determine a preferred communication vector for each IMD. However, before providing addition details of the specific embodiments of the present technology, an example environment in which embodiments of the present technology can be useful will first be described with reference to FIGS. 1-3. More specifically, FIGS. 1-3 will be used to describe an example cardiac pacing system, wherein pacing and sensing operations can be performed by multiple IMDs. Such IMDs may include one or more leadless cardiac pacemakers, an implantable cardioverter defibrillator (ICD), such as a non-vascular ICD (NV-ICD), an insertable cardiac monitor (ICM), and an external programmer to reliably and safely coordinate pacing and/or sensing operations. A leadless cardiac pacemaker can also be referred to more succinctly herein as a leadless pacemaker (LP). Where the system includes an ICD, the system is also capable of performing defibrillation. Where the only IMD is an ICM, the system may only be capable of performing monitoring without performing any therapy.

Figure 1:
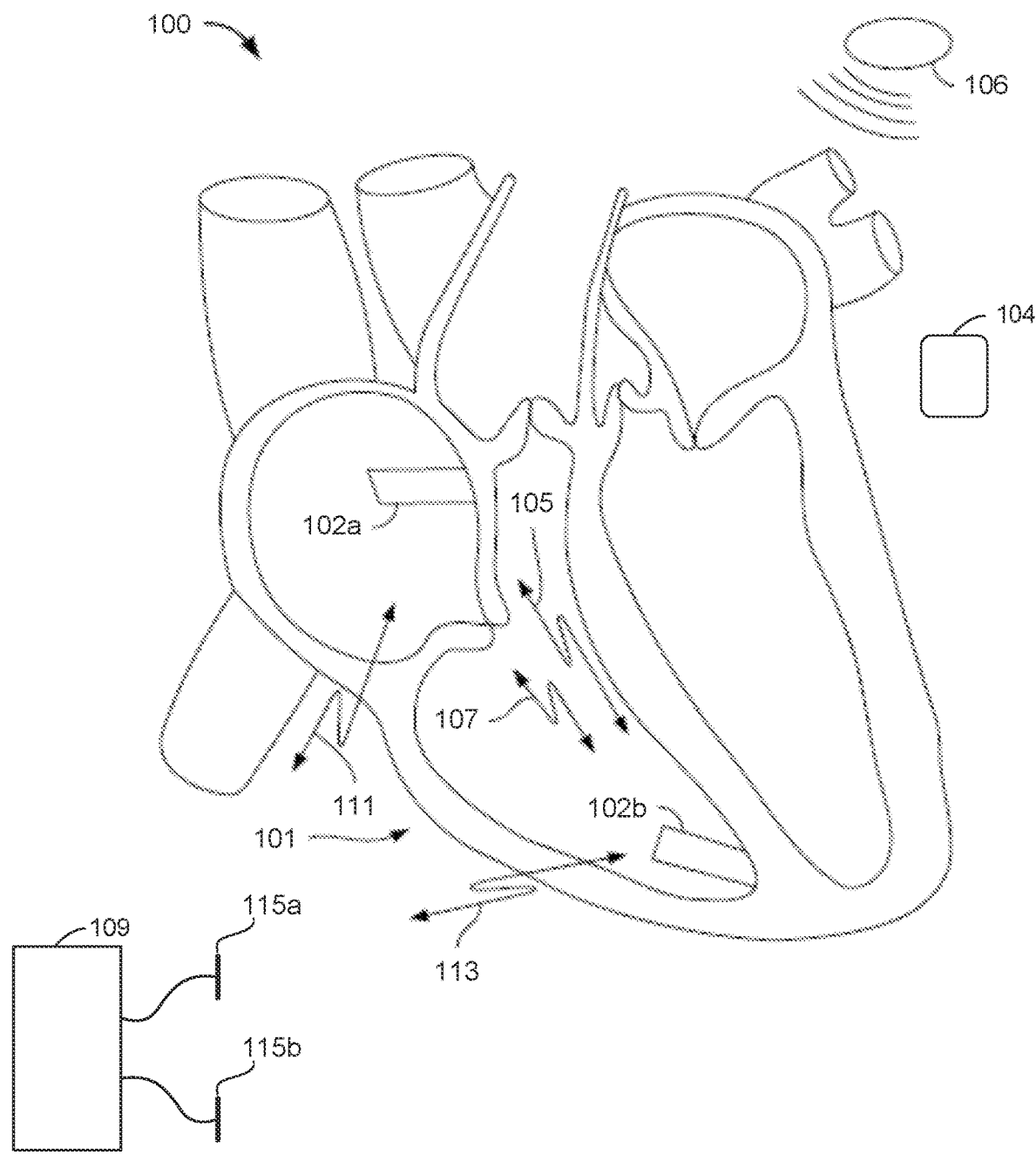
FIG. 1 illustrates a system that includes a plurality of implantable medical devices that are implanted in a patent and an external programmer that can be used to program and/otherwise communicate with the implantable devices. The external programmer in FIG. 1 is an example of an external device.

FIG. 1 illustrates a system 100 that is configured to be at least partially implanted in a heart 101. The system 100 includes LPs 102a and 102b located in different chambers of the heart 101. The LP 102a is located in a right atrium, while LP 102b is located in a right ventricle. The LPs 102a and 102b can communicate with one another to inform one another of various local physiologic activities, such as local intrinsic events, local paced events, and/or the like. The LPs 102a and 102b may be constructed in a similar manner, but operate differently based upon which chamber LP 102a or 102*b* is located. The LPs 102*a* and 102*b* may sometimes be referred to collectively herein as the LPs 102, or individually as an LP 102.

In certain embodiments, the LPs 102*a* and 102*b* communicate with one another, and/or with an ICM 104, and/or with an ICD 106, by conductive communication through the same electrodes that are used for sensing and/or delivery of pacing therapy. The LPs 102*a* and 102*b* also use conductive communication to communicate with a non-implanted device, e.g., an external programmer 109, having two electrodes 115*a* and 115*b* placed on the skin of a patient within which the LPs 102*a* and 102*b* are implanted. While not shown (and not preferred, since it would increase the size and power consumption of the LPs 102*a* and 102*b*), the LPs 102*a* and 102*b* can potentially include an antenna and/or telemetry coil that would enable them to communicate with one another, the ICD 106 and/or a non-implanted device using RF and/or inductive communication. While only two LPs 102 are shown in FIG. 1, it is possible that more than two LPs can be implanted in a patient. For example, to provide for bi-ventricular pacing and/or cardiac resynchronization therapy (CRT), in addition to having LPs implanted in or on the right atrial (RA) chamber and the right ventricular (RV) chamber, a further LP can be implanted in or on the left ventricular (LV) chamber. It is also possible that a single LP be implanted within a patient, e.g., in or on the RV chamber, the RA chamber, or the LV chamber, but not limited thereto. It would also be possible for more than one LP to be implanted in or on a same cardiac chamber.

In some embodiments, one or more of the LPs 102*a*, 102*b* can be co-implanted with the ICM 104 and/or the ICD 106. In such embodiments, the ICM 104 and/or the ICD 106 are examples of other types of IMDs that may need to communicate with an external device, such as an external programmer, from time to time. The ICM 104 and/or the ICD 106 may utilize conductive communication to communicate with the LPs 102, as well as to communicate with an external device. It may alternatively or additionally be possible for the ICM 104 and/or the ICD 106 to utilize radio frequency (RF) communication and/or inductive communication to communicate with an external device, depending upon the specific implementation, and depending upon the capabilities of the external device.

Each LP 102*a*, 102*b* uses two or more electrodes located within, on, or within a few centimeters of the housing of the pacemaker, for pacing and sensing at the cardiac chamber, for bidirectional conductive communication with one another, with the programmer 109, the ICD 106, and/or the ICM 104. Such an ICM 104 can be intended for subcutaneous implantation at a site near the heart 101. The ICM 104 can include, for example, a pair of spaced-apart sense electrodes positioned with respect to a housing, wherein the sense electrodes provide for detection of far-field EGM signals, and can also be used for conductive communication with one or more other implanted devices, such as the LP(s) 102*a* and/or 102*b* and/or the ICD 106. Such an ICM can also include an antenna that is configured to wirelessly communicate with an external device, such as an external programmer 109, in accordance with one or more wireless communication protocols (e.g., Bluetooth, Bluetooth low energy, Wi-Fi, etc.). The housing of the ICM 104 can include various other components such as: sense electronics for receiving signals from the electrodes, a microprocessor for processing the signals in accordance with algorithms, a loop memory for temporary storage of cardiac activity (CA) data, a device memory for long-term storage of CA data upon certain triggering events, sensors for detecting patient activity and a battery for powering components.

Each LP 102*a*, 102*b* and/or other type of IMD can transmit an advertisement sequence of pulses using at least two electrodes of the IMD (e.g., LP) from time to time so that an external device (e.g., an external programmer, or a remote monitor) that has or is communicatively coupled to external electrodes that are in contact with the patient (within which the LP(s) and/or other IMD(s) is/are implanted) can detect the presence of the IMD(s) and optionally establish a communication session with one or more IMD(s). For a more specific example, an LP (or other type of IMD) can transmit an advertisement sequence of pulses every specified number of cardiac cycles (e.g., every eight cardiac cycles), or every specified period of time (e.g., every 5 seconds), but not limited thereto. In accordance with certain embodiments, the advertisement sequence of pulses is a predetermined sequence of pulses that indicates to an external device (e.g., an external programmer, or a remote monitor) that an LP (or other type of IMD) is implanted within a patient. The advertisement sequence of pulses can also be referred to as a sniff sequence of pulses, or more succinctly as a sniff. In accordance with certain embodiments of the present technology, which are described below, an external device can use the sniff pulses to identify which one of a plurality of communication vectors is a preferred communication vector for communicating with the IMD that transmitted the sniff pulses. For example, where the external device has or is communicatively coupled to three external electrodes, i.e., first, second, and third external electrodes, the external device can test and select among first, second, and third subsets of the external electrodes, wherein the first subset includes the first and second external electrodes, the second subset includes the first and third external electrodes, and the third subset includes the second and third external electrodes.

Figure 2:
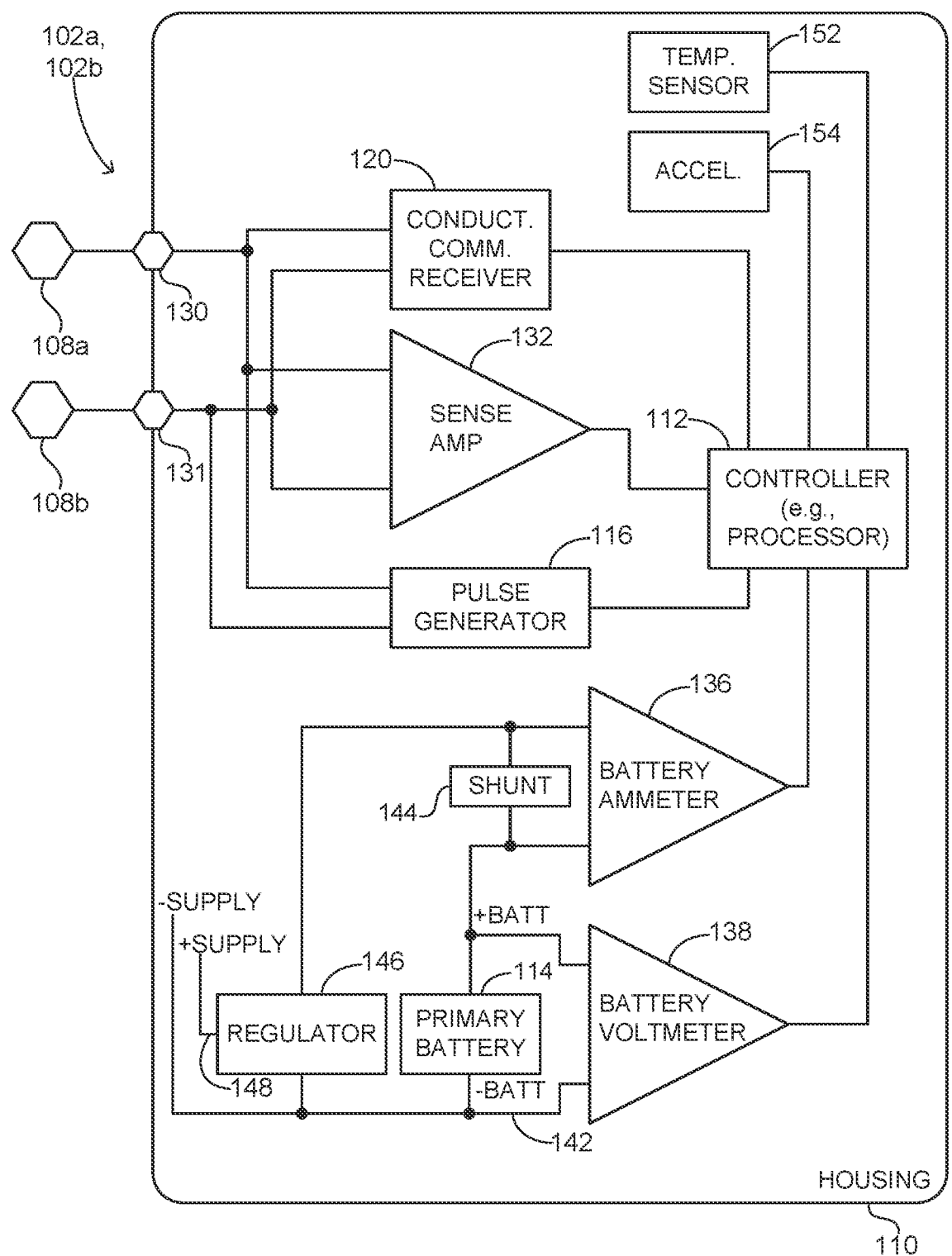
FIG. 2 is a high level block diagram of an example LP.

Referring to FIG. 2, a block diagram shows an example embodiment for portions of the electronics within the LPs 102*a*, 102*b* configured to provide conductive communication through the same electrodes that are used for cardiac pacing and/or sensing. Each of the LPs 102*a*, 102*b* includes at least two leadless electrodes configured for delivering cardiac pacing pulses, sensing evoked and/or natural cardiac electrical signals, and uni-directional and/or bi-directional communication. In FIG. 2 (and FIG. 3) the two electrodes shown therein are labeled 108*a* and 108*b*. Such electrodes can be referred to collectively as the electrodes 108, or individually as an electrode 108. An LP 102, or other type of IMD, can include more than two electrodes, depending upon implementation.

In FIG. 2, each of the LPs 102*a*, 102*b* is shown as including a conductive communication receiver 120 that is coupled to the electrodes 108 and configured to receive conductive communication signals from the other LP 102, the ICM 104 and/or the ICD 106, but not limited thereto. The conductive communication receiver 120 and the electrodes 108 can also be used to receive conductive communication signals from the external programmer 109, and/or another type of external device. Although one receiver 120 is depicted in FIG. 2, in other embodiments, each LP 102*a*, 102*b* may also include one or more additional receivers. As will be described in additional detail below, the pulse generator 116 can function as a transmitter that transmits conductive communication signals using the electrodes 108, under the control of the controller 112. In certain embodiments, the LPs 102*a*, 102*b* may communicate over more than just first and second communication channels 105 and 107. In certain embodiments, the LPs 102a, 102b may communicate over one common communication channel 105. More specifically, the LPs 102a and 102b can communicate conductively over a common physical channel via the same electrodes 108 that are also used to deliver pacing pulses. Usage of the electrodes 108 for conductive communication enables the one or more LPs 102a, 102b to perform antenna-less and inductive coil-less communication. Where multiple implantable devices (such as the LPs 102a and 102b) communicate with one another using conductive communication, such conductive communication can be referred to as implant-to-implant (i2i) conductive communication, or more succinctly, as i2i conductive communication.

Optionally, an LP (or other IMD) that receives any conductive communication signal from another LP (or other IMD) or from a non-implanted device (e.g., a programmer 109) may transmit a receive acknowledgement indicating that the receiving LP (or other IMD, or external device) received the conductive communication signal. In certain embodiments, where an IMD expects to receive a conductive communication signal within a window, and fails to receive the conductive communication signal within the window, the IMD may transmit a failure-to-receive acknowledgement indicating that the receiving IMD failed to receive the conductive communication signal. Other variations are also possible and within the scope of the embodiments described herein. Each conductive communication signal can include one or more sequences of conductive communication pulses. In accordance with certain embodiments, conductive communication pulses are delivered during cardiac refractory periods that are identified or detected by the LP(s) and/or other IMD(s). In accordance with certain embodiments, conductive communication pulses are sub-threshold, i.e., they are below the capture threshold for the patient.

The LPs 102a, 102b can exchange event messages within i2i conductive communication signals to enable synchronized therapy and additional supportive features (e.g., measurements, etc.). To maintain synchronous therapy, each of the LPs 102a, 102b is made aware (through the event messages) when an event occurs in the chamber containing the other LP 102a, 102b. Example additional details of i2i event messages that are sent between LPs 102 are provided in U.S. patent application Ser. No. 17/222,242, filed Apr. 5, 2021, titled REMOTE FOLLOW-UP METHODS, SYSTEMS, AND DEVICES FOR LEADLESS PACEMAKER SYSTEMS, which is incorporated herein by reference above.

For synchronous event signaling, LPs 102a and 102b may maintain synchronization and regularly communicate at a specific interval. Synchronous event signaling allows the transmitter and receiver in each LP 102a, 102b to use limited (or minimal) power as each LP 102a, 102b is only powered for a small fraction of the time in connection with transmission and reception. For example, LP 102a, 102b may transmit/receive (Tx/Rx) communication messages in time slots having duration of 10-20 μs, where the Tx/Rx time slots occur periodically (e.g., every 10-20 ms). Such time slots can also be referred to as windows.

Still referring to FIG. 2, each LP 102a, 102b is shown as including a controller 112 and a pulse generator 116. The controller 112 can include, e.g., a microprocessor (or equivalent control circuitry), RAM and/or ROM memory, logic and timing circuitry, state machine circuitry, and I/O circuitry, but is not limited thereto. The controller 112 can further include, e.g., timing control circuitry to control the timing of the stimulation pulses (e.g., pacing rate, atrio-ventricular (AV) delay, atrial interconduction (A-A) delay, or ventricular interconduction (V-V) delay, etc.). Such timing control circuitry may also be used for the timing of refractory periods, blanking intervals, noise detection windows, evoked response windows, alert intervals, marker channel timing, and so on. The controller 112 can further include other dedicated circuitry and/or firmware/software components that assist in monitoring various conditions of the patient's heart and managing pacing therapies. The controller 112 and the pulse generator 116 may be configured to transmit event messages, via the electrodes 108, in a manner that does not inadvertently capture the heart in the chamber where LP 102a, 102b is located, such as when the associated chamber is not in a refractory state. In addition, a LP 102a, 102b that receives an event message may enter an "event refractory" state (or event blanking state) following receipt of the event message. The event refractory/blanking state may be set to extend for a determined period of time after receipt of an event message in order to avoid the receiving LP 102a, 102b from inadvertently sensing another signal as an event message that might otherwise cause retriggering. For example, the receiving LP 102a, 102b may detect a measurement pulse from another LP 102a, 102b or programmer 109.

In accordance with certain embodiments herein, the external programmer 109 may communicate over a programmer-to-LP channel, with LPs 102a, 102b utilizing the same communication scheme. The external programmer 109 may listen to the event message transmitted between LPs 102a, 102b and synchronize programmer to implant communication such that the external programmer 109 does not transmit communication signals 113 until after an implant to implant messaging sequence is completed.

In some embodiments, an individual LP 102 can comprise a hermetic housing 110 configured for placement on or attachment to the inside or outside of a cardiac chamber and at least two leadless electrodes 108 proximal to the housing 110 and configured for conductive communication with at least one other device within or outside the body. Depending upon the specific implementation, and/or the other device with which an LP is communicating, the conductive communication may be unidirectional or bi-directional.

FIG. 2 depicts a single LP 102a (or 102b) and shows the LP's functional elements substantially enclosed in a hermetic housing 110. The LP 102a (or 102b) has at least two electrodes 108 located within, on, or near the housing 110, for delivering pacing pulses to and sensing electrical activity from the muscle of the cardiac chamber, and for conductive communication with at least one other device within or outside the body. Hermetic feedthroughs 130, 131 conduct electrode signals through the housing 110. The housing 110 contains a primary battery 114 to supply power for pacing, sensing, and communication. The housing 110 also contains circuits 132 for sensing cardiac activity from the electrodes 108, receiver 120 for receiving information from at least one other device via the electrodes 108, and the pulse generator 116 for generating pacing pulses for delivery via the electrodes 108 and also for transmitting information to at least one other device via the electrodes 108. The housing 110 can further contain circuits for monitoring device health, for example a battery current monitor 136 and a battery voltage monitor 138, and can contain circuits for controlling operations in a predetermined manner.

The electrodes 108 can be configured to communicate bidirectionally among the multiple leadless cardiac pacemakers, the implanted ICD 106 and/or the implanted ICM 104 to coordinate pacing pulse delivery and optionally other therapeutic or diagnostic features using messages that identify an event at an individual pacemaker originating the message and a pacemaker receiving the message react as directed by the message depending on the origin of the message. An LP 102a, 102b that receives the event message reacts as directed by the event message depending on the message origin or location. In some embodiments or conditions, the two or more leadless electrodes 108 can be configured to communicate bidirectionally among the one or more LPs, the ICD 106, and/or the ICM 104 and transmit data including designated codes for events detected or created by an individual pacemaker. Individual pacemakers can be configured to issue a unique code corresponding to an event type and a location of the sending pacemaker. The electrodes can also be used to transmit and/or receive conductive communication signals from an external device.

As shown in FIG. 2, each LP 102a, 102b can comprise two (or more) leadless electrodes 108 configured for delivering cardiac pacing pulses, sensing evoked and/or natural cardiac electrical signals, and bidirectionally communicating with one another and/or the co-implanted ICD 106. As shown in FIG. 2, the primary battery 114 has positive terminal 140 and negative terminal 142. Current from the positive terminal 140 of primary battery 114 flows through a shunt 144 to a regulator circuit 146 to create a positive voltage supply 148 suitable for powering the remaining circuitry of the pacemaker 102. The shunt 144 enables the battery current monitor 136 to provide the controller 112 with an indication of battery current drain and indirectly of device health. The illustrative power supply can be a primary battery 114. The LP is also shown as including a temperature sensor 152 and an accelerometer 154.

In various embodiments, each LP 102a, 102b can manage power consumption to draw limited power from the battery, thereby reducing device volume. Each circuit in the system can be designed to avoid large peak currents. For example, cardiac pacing can be achieved by discharging a tank capacitor (not shown) across the pacing electrodes. Recharging of the tank capacitor is typically controlled by a charge pump circuit. In a particular embodiment, the charge pump circuit is throttled to recharge the tank capacitor at constant power from the battery.

In some embodiments, the controller 112 in one LP 102 can access signals on the electrodes 108 and can examine output pulse duration from another pacemaker for usage as a signature for determining triggering information validity and, for a signature arriving within predetermined limits, activating delivery of a pacing pulse following a predetermined delay of zero or more milliseconds. The predetermined delay can be preset at manufacture, programmed via an external programmer, or determined by adaptive monitoring to facilitate recognition of the triggering signal and discriminating the triggering signal from noise. In some embodiments or in some conditions, the controller 112 can examine output pulse waveform from another leadless cardiac pacemaker for usage as a signature for determining triggering information validity and, for a signature arriving within predetermined limits, activating delivery of a pacing pulse following a predetermined delay of zero or more milliseconds.

Figure 3:
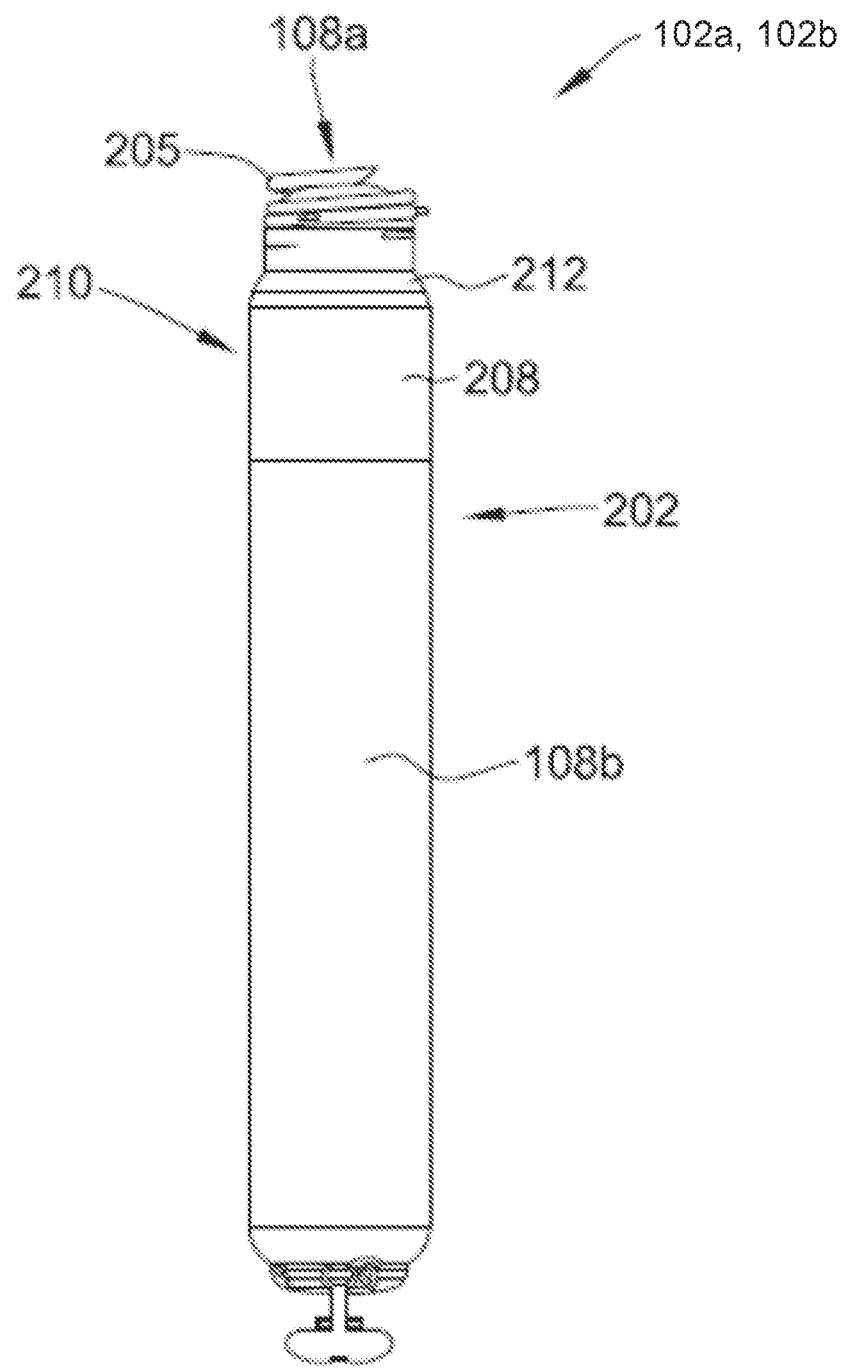
FIG. 3 illustrates an example form factor for an LP.

FIG. 3 shows an example form factor of an LP 102a, 102b. The LP can include a hermetic housing 202 (110) with electrodes 108a and 108b disposed thereon. As shown, electrode 108a can be separated from but surrounded partially by a fixation mechanism 205, and the electrode 108b can be disposed on the housing 202. The fixation mechanism 205 can be a fixation helix, a plurality of hooks, barbs, or other attaching features configured to attach the pacemaker to tissue, such as heart tissue. The electrodes 108a and 108b are examples of the electrodes 108 shown in and discussed above with reference to FIG. 2. The housing can also include an electronics compartment 210 within the housing that contains the electronic components necessary for operation of the pacemaker, including, e.g., a pulse generator, receiver, a battery, and a processor for operation. The hermetic housing 202 can be adapted to be implanted on or in a human heart, and can be cylindrically shaped, rectangular, spherical, or any other appropriate shapes, for example. The housing can comprise a conductive, biocompatible, inert, and anodically safe material such as titanium, 316L stainless steel, or other similar materials. The housing 202 can further comprise an insulator disposed on the conductive material to separate electrodes 108a and 108b. The insulator can be an insulative coating on a portion of the housing between the electrodes, and can comprise materials such as silicone, polyurethane, parylene, or another biocompatible electrical insulator commonly used for implantable medical devices. In the embodiment of FIG. 3, a single insulator 208 is disposed along the portion of the housing between electrodes 108a and 108b. In some embodiments, the housing itself can comprise an insulator instead of a conductor, such as an alumina ceramic or other similar materials, and the electrodes can be disposed upon the housing.

As shown in FIG. 3, the pacemaker can further include a header assembly 212 to isolate electrodes 108a and 108b. The header assembly 212 can be made from PEEK, tecothane or another biocompatible plastic, and can contain a ceramic to metal feedthrough, a glass to metal feedthrough, or other appropriate feedthrough insulator as known in the art. The term metal, as used herein, also encompasses alloys that are electrically conductive. The electrodes 108a and 108b can comprise pace/sense electrodes, or return electrodes. A low-polarization coating can be applied to the electrodes, such as sintered platinum, platinum-iridium, iridium, iridium-oxide, titanium-nitride, carbon, or other materials commonly used to reduce polarization effects, for example. In FIG. 3, electrode 108a can be a pace/sense electrode and electrode 108b can be a return electrode. The electrode 108b can be a portion of the conductive housing 202 that does not include an insulator 208.

Several techniques and structures can be used for attaching the housing 202 to the interior or exterior wall of the heart. A helical fixation mechanism 205, can enable insertion of the device endocardially or epicardially through a guiding catheter. A torqueable catheter can be used to rotate the housing and force the fixation device into heart tissue, thus affixing the fixation device (and also the electrode 108a in FIG. 2) into contact with stimulable tissue. Electrode 108b can serve as an indifferent electrode for sensing and pacing. The fixation mechanism may be coated partially or in full for electrical insulation, and a steroid-eluting matrix may be included on or near the device to minimize fibrotic reaction, as is known in conventional pacing electrode-leads.

Figure 4:
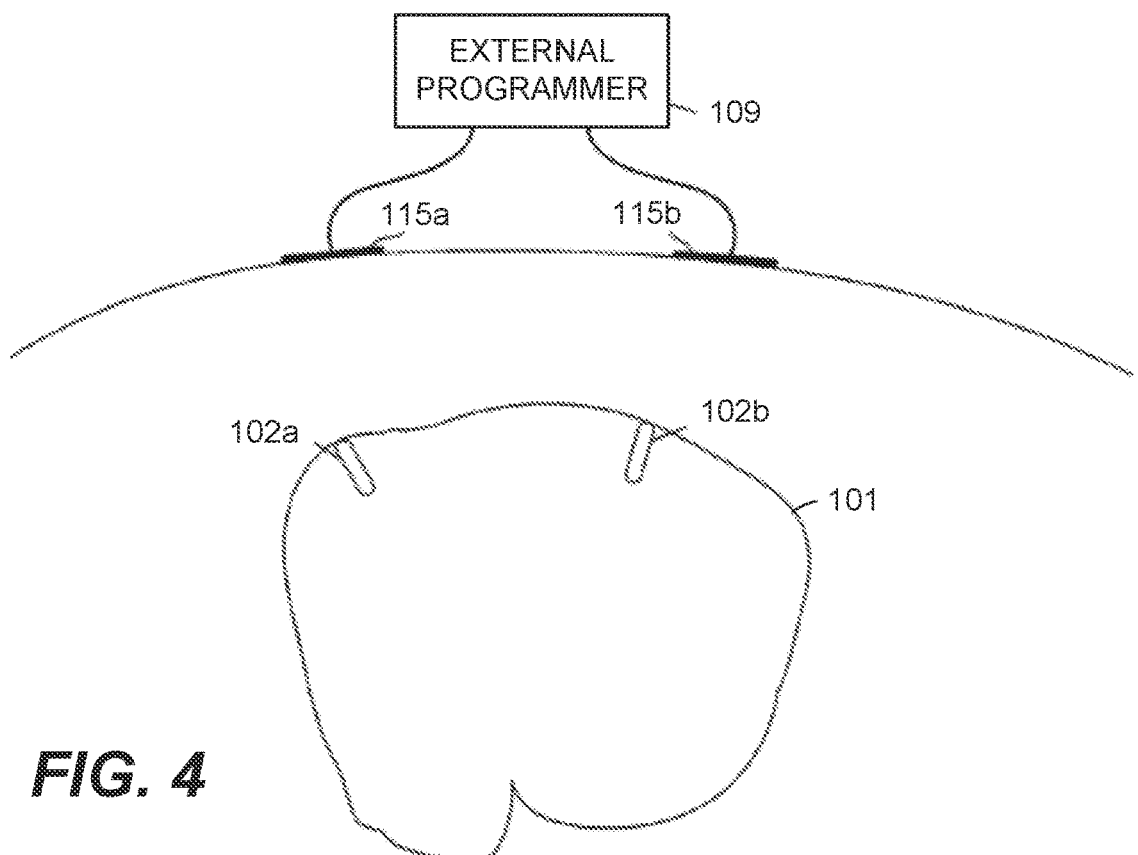
FIG. 4 depicts a sample configuration involving an external programmer and two endocardially implanted LPs.
Figure 5:
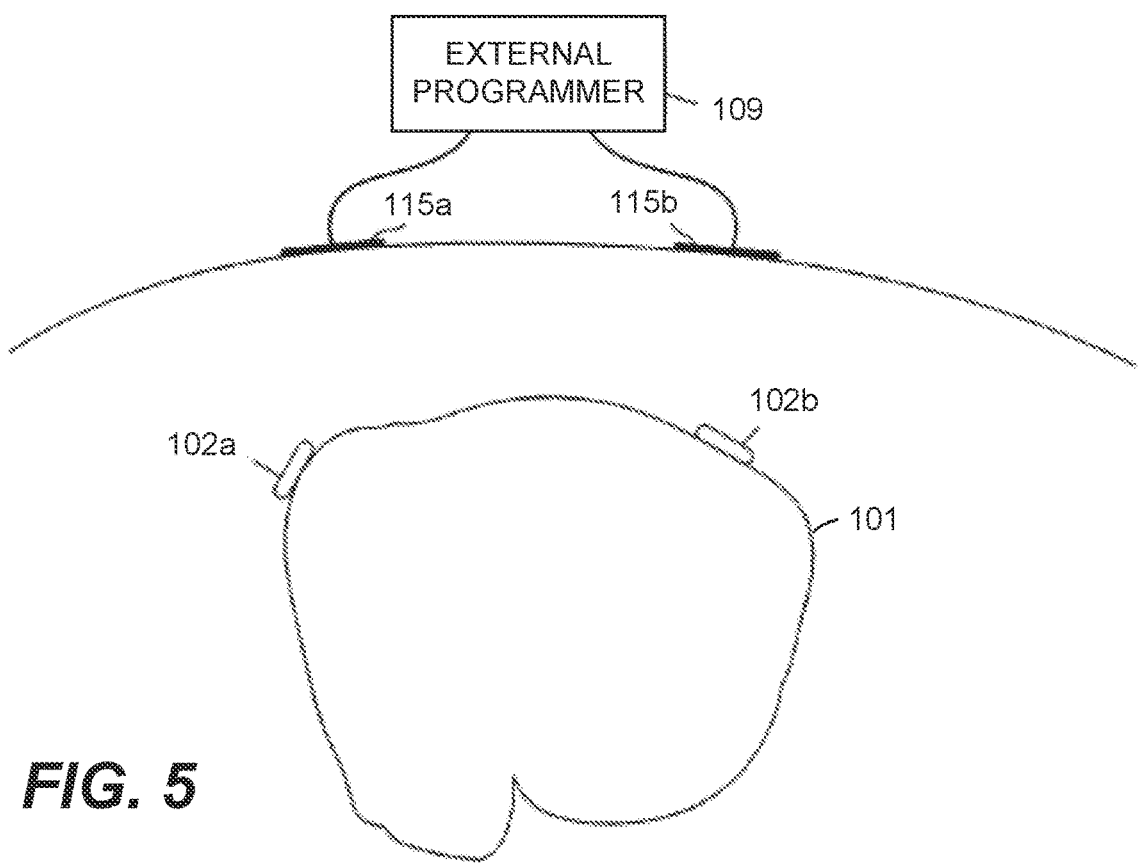
FIG. 5 depicts a sample configuration involving an external programmer and two LPs implanted epicardially (on the external heart surface).

FIGS. 4 and 5 are schematic pictorial views depicting how an external programmer 109 coupled to two skin electrodes 115a, 115b can communicate with the LP 102a and/or the LP 102b via conductive communication, which is also referred to interchangeably herein as conducted communication. Such communication may take place via bidirectional communication pathways comprising a receiving pathway that decodes information encoded on pulses generated by one or more of the LPs 102a or 102b and conductive through body tissue to the external programmer 109. According to the illustrative arrangement, the bidirectional communication pathways can be configured for communication with multiple LPs 102a and 102b via two or more electrodes and conduction through body tissue.

The external programmer 109 is connected by a communication transmission channel and has transmitting and receiving functional elements for a bi-directional exchange of information with one or more IMDs, such as LP 102a and/or LP 102b. The communication channel includes two external electrodes 115a and 115b which can be affixed or secured to the surface of the skin. From the point of the skin, the communication transmission channel is wireless, includes the ion medium of the intra- and extra-cellular body liquids, and enables electrolytic-galvanic coupling between the external electrodes, which can also be referred to as surface electrodes, and the LPs, or more generally, IMDs. The bidirectional communication pathways can further comprise a transmitting pathway that passes information from the external programmer 109 to one or more of the LPs 102a and/or 102b by direct conduction through the body tissue by modulation that avoids skeletal muscle stimulation using modulated signals at a frequency in a range from approximately 10 kHz to 100 kHz, or at higher frequencies. For example, p2i communication signals may be transmitted at a center frequency (fc) of 500 kHz.

Information transmitted from the external programmer 109 to the implanted LPs is conveyed by modulated signals at the approximate range of 10 kHz to 100 kHz which is a medium-high frequency, or at higher frequencies. The signals are passed through the communication transmission channel by direct conduction. A modulated signal in the frequency range has a sufficiently high frequency to avoid any depolarization within the living body which would lead to activation of the skeletal muscles and discomfort to the patient. The frequency is also low enough to avoid causing problems with radiation, crosstalk, and excessive attenuation by body tissue. Thus, information may be communicated at any time, without regard to the heart cycle or other bodily processes. The use of other frequency ranges is also possible and within the scope of the embodiments described herein.

FIG. 4 depicts a sample configuration involving the external programmer 109 and two endocardially implanted LPs 102a and 102b. The external programmer 109 is physically connected to the skin surface via two external electrodes 115a and 115b (also referred to as surface electrodes), which can serve three functions. The external electrodes 115a and 115b can be referred to individually as an external electrode 115 (or a surface electrode 115), or collectively as external electrodes 115 (or surface electrodes 115). First, the electrodes 115 can be used transmit encoded information from the programmer 109 to the LPs or other IMD(s) using a modulated signal, e.g., at a medium frequency 10 kHz to 100 kHz. Second, the external electrodes 115 can be used to receive information from individual LPs or other IMD(s) by detecting encoded information in the pacing pulses of the LP(s). Third, the external electrodes 115 can receive or sense a surface electrocardiogram for display and analysis by the programmer 109.

In FIG. 4, the two LPs 102a and 102b are implanted within the heart 101 endocardially. Alternatively, as shown in FIG. 5, the two LPs 102a and 102b can be implanted by affixing to the exterior surface of the heart 101. The external electrodes 115 and the external programmer 109 function similarly in arrangements shown in FIGS. 4 and 5 whether the LPs 102a and 102b are implanted endocardially or epicardially (on the external heart surface). No restriction is imposed that the LPs are all implanted inside or all implanted outside the heart. One or more may be implanted endocardially along with others implanted on the outer surface of the heart. The functioning of the programmer 109 is substantially the same.

As explained above in the Background, a potential problem with using conductive communication signals to provide for communication between an external device and one or more IMDs, is that the orientation of the IMD(s) can cause fading that can adversely affect conductive communication. Additionally, the locations of the two external electrodes, which define a communication vector for the external device, may not provide for good communication signal quality between the external device and an IMD. These problems may be exacerbated when there is a need or desire for the external device to communicate with multiple (i.e., two or more) IMDs. For example, it may be the case that a communication vector associated with two external electrodes attached to a patient's skin provides for good conductive communication signal quality with only one of multiple IMDs. To overcome this problem, the two externals electrode attached to the patient's skin at first locations can first be used to provide for conductive communication between the external device and a first IMD. The two external electrodes can then be moved to second locations and then used to provide for conductive communication between the external device and a second IMD. If the patient also includes a third IMD, the two external electrodes can then be moved to third locations and then used to provide for conductive communication between the external device and the third IMD. Even if a patient only includes a single IMD, it still may be necessary to move one or both of the two external electrodes one or more times before an acceptable conductive communication signal quality is achieved between an external device and the signal IMD. This repositioning or moving of the two external electrodes can be time consuming for both the patient and the medical personnel, as well as costly to the patient in terms of increasing their medical bills.

Use of Multiple Communication Vectors

Certain embodiments of the present technology described herein can be used improve (and preferably optimize) conductive communication signal quality between an external device (e.g., an external programmer or a remote monitor) and each of one or more IMDs by dynamically switching between multiple electrode combinations (e.g., pairs) to find a preferred communication vector for use with each of the IMDs. Certain embodiments described herein assess the communication signal quality for a given communication vector, and criteria are used to determine a preferred communication vector for each IMD. In order for an external device to be able to select among different communication vectors for performing conductive communication with one or more IMDs, the external device should include or be communicatively coupled to at least three external electrodes that are in contact with a patient, within which the one or more IMDs is/are implanted. An example of this is shown in FIG. 6.

Figure 6:
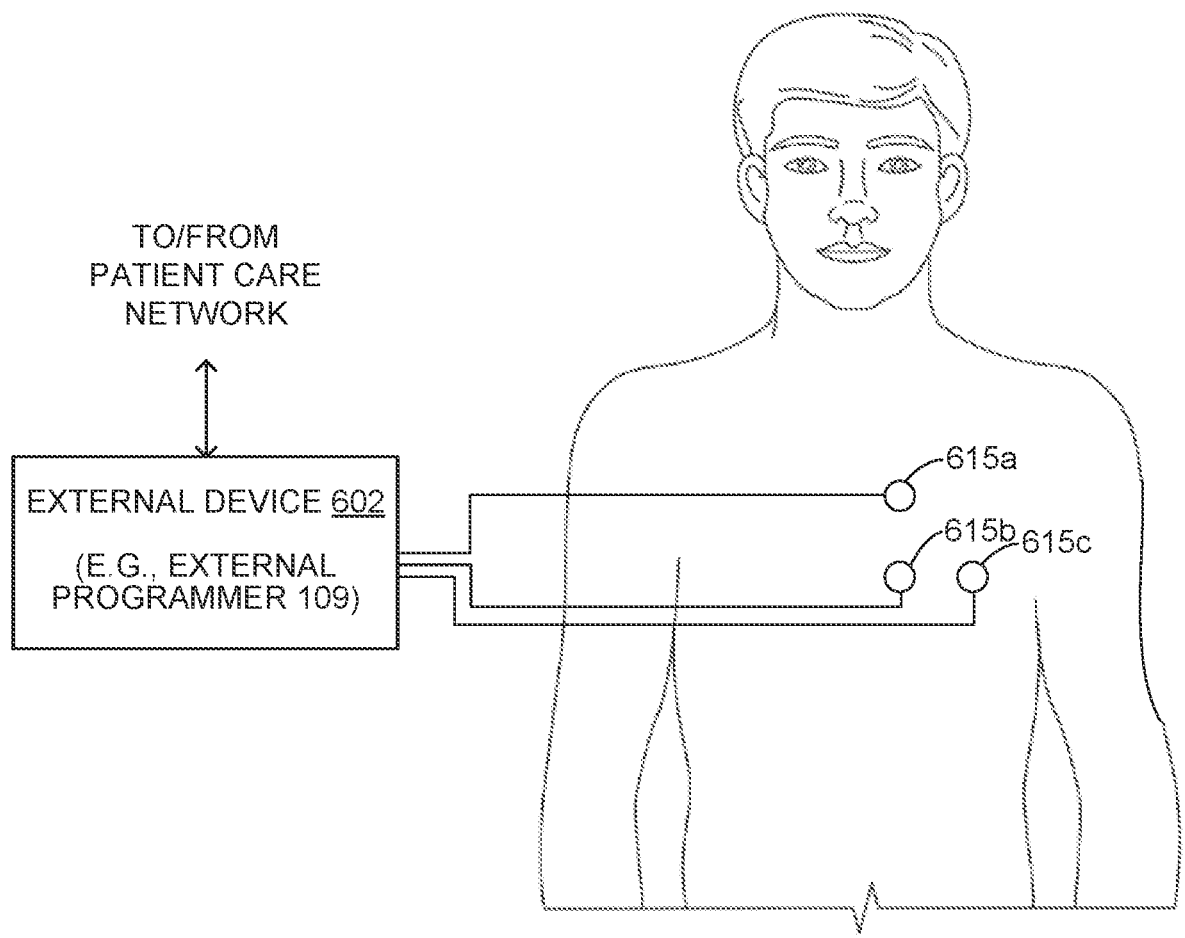
FIG. 6 depicts an example of an external device communicatively coupled to three electrodes that are in contact with the chest of a patient.

Referring to FIG. 6, an external device 602 is shown as being communicatively coupled to three external electrodes 615a, 615b, and 615c, which can be referred to collectively as the external electrodes 615, or individually as an external electrode 615. In FIG. 6 the external electrodes 615 are shown as being in contact with the chest of a patient, however, that need not be the case. Alternatively, one or more external electrodes can be in contact with the back of the patient, and/or with limbs or digits of the patient, but are not limited thereto. The external electrodes 615 can be physically separated from one another to thereby enable each of the electrodes to be independently placed in contact with the patient's skin at any desired location. Alternatively, the external electrodes 615, while electrically isolated from one another, can be physically attached to a same patch or substrate, e.g., a triangular or Y-shaped patch, or the like, that can be configured to be placed on a patient's chest or back, but not limited thereto. The external device 602 can optionally be communicatively coupled to a remote patient care network, e.g., via one or more wired and/or wireless communication network(s). Example details of the external device 602 are described below with reference to FIG. 7.

Figure 7:
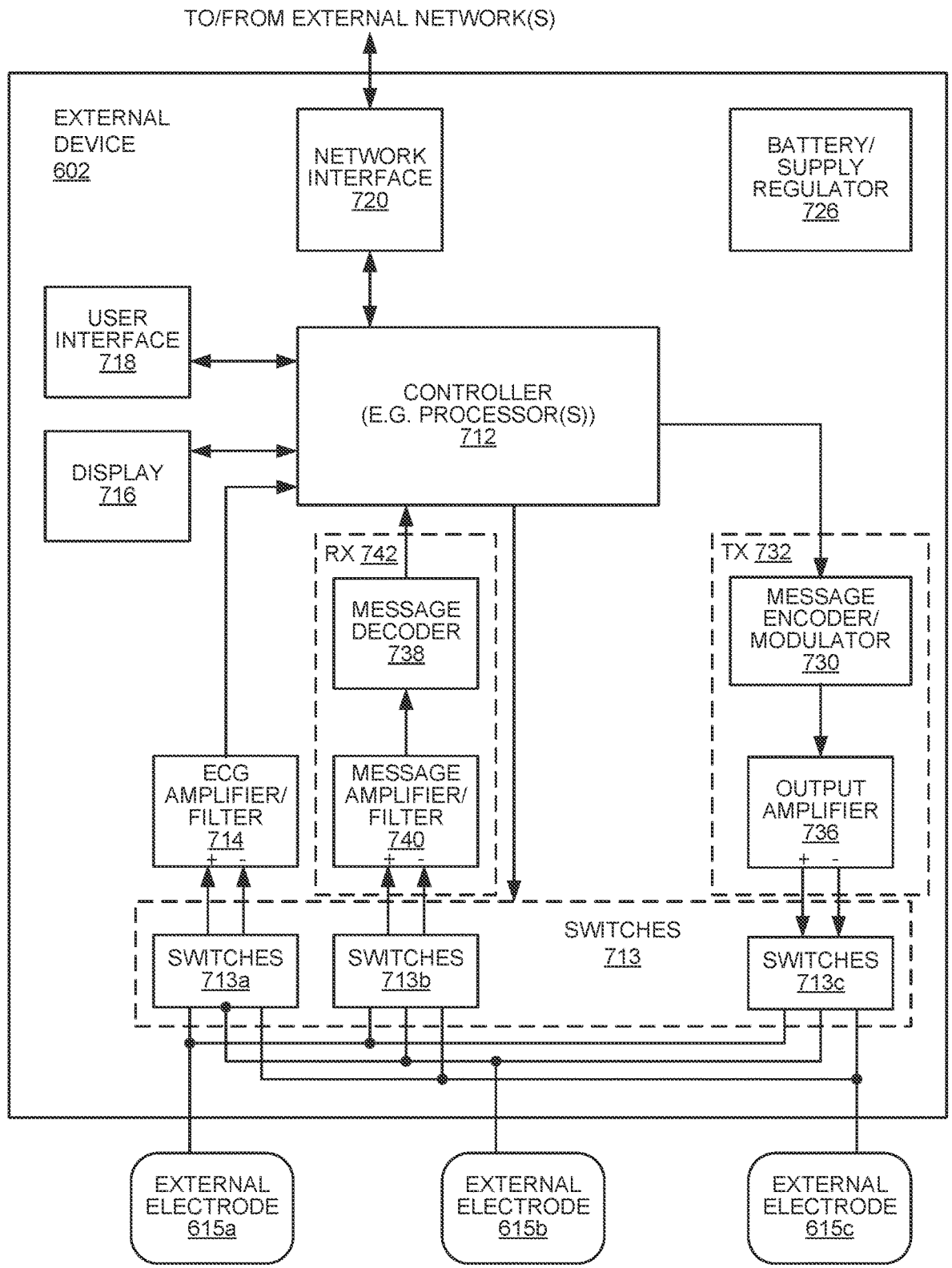
FIG. 7 is a high level block diagram illustrating example details of an external device that is configured to communicate with one or more IMDs implanted within a patient using conductive communication, wherein the external device includes or is communicatively coupled to at least three external electrodes that are in contact with the patient.

Referring to FIG. 7, shown therein is an example block diagram of the external device 602 (e.g., the external programmer 109, or a remote monitor), which is configured to communicate with one or more IMDs implanted within a patient using conductive communication, wherein the external device 602 includes or is communicatively coupled to at least three external electrodes 615 that are in contact with the patient.

Where the external device 602 is an external programmer (e.g., 109), the external device is capable of programming one or more IMDs, such as one or more LPs, an ICM and/or an ICD. The external device 602 can also be used to obtain diagnostic information from one or more IMDs. Where the external device 602 is a remote monitor, it may not be capable of programming any IMDs. The external device 602 is shown as including a controller 712, a display 716, a user interface 718, a network interface 720, and a battery/supply regulator 726. The battery and/or supply regulator 726 provides one or more constant voltages to the various components of the external device 602 during normal operation. The external device 602 is also shown as including an ECG amplifier and/or filter 714, a conductive communication receiver (RX) 742, and a conductive communication transmitter (TX) 732. The receiver 742, in this example embodiment, is shown as including a message amplifier and/or filter 740, and a message decoder 738, and is configured to receive conductive communication signals from one or more LPs (e.g., 102a and/or 102b). The controller 712, which is used to control the operation of the external device 702, can include, e.g., one or more processors (or equivalent control circuitry), RAM and/or ROM memory, logic and timing circuitry, state machine circuitry, and/or I/O circuitry, but is not limited thereto. The controller 712 can also include a clock circuit, or a separate clock circuit (not shown) can provide a clock signal to the controller 712.

In the embodiment shown in FIG. 7, the external device 602 is shown as being connected to three external electrodes 615a, 615b, and 615c, which can be referred to collectively as the electrodes 615, or individually as an electrode 615. The electrodes 615 are shown as being connected to switches 713, which are shown as including first, second, and third sets of switches 713a, 713b, and 713c. The external electrodes 615 can be located on a housing of the external device 602, or can be separate from such a housing. Where the electrodes 615 are separate from a housing of the external device 602, each of the electrodes 615 can be attached to a separate respective wire, or the electrodes 615 can be attached to a further housing that is communicatively coupled to the external device 602 via one or more wires, or via a wireless connection, e.g., using Bluetooth or WiFi, but not limited thereto. Other variations are also possible and within the scope of the embodiments described herein. The external electrodes 615, as will be described in more detail below, can be used to transmit and receive conductive communication signals to/from one or more LPs, and/or one or more other types of IMDs, and optionally can also be used to sense an electrocardiogram (ECG).

The external electrodes 615 are intended to come into contact with the skin of a patient. For example, the external electrodes can be skin electrodes that are configured to be attached to a patient's torso (e.g., chest and/or back) via an adhesive and/or gel. For another example, the external electrodes 615 can be configured to be touched by one or more digits on each hand of a patient, or to come into contact with a patient's wrist, a patient's limb, or a patient's chest, but are not limited thereto. A set of switches 713a is connected between the electrodes 615 and the ECG amplifier and/or filter 714, a set of switches 714b is connected between the electrodes 615 and the receiver 742, and a further set of switches 713c is connected between the electrodes 615 and the transmitter 732. The various sets of switches are controlled by the controller 712. In certain embodiments, the amplifiers and/or filters 714, 740, and 736 are each differential circuits that are intended to be connected to a pair of the electrodes 615 by the switches 713 under the control of the controller 712. For an example, the switches 713b can be controlled to connect any pair of the electrodes 615a, 615b, 615c to the message amplifier and/or filter 740. For an example, the switches 713b can connected the electrode 615a to a first input of the message amplifier/filter 740, and connect the electrode 615b to a second input of the message amplifier/filter 740, and not connect electrode 615c to any input of the message amplifier/filter 740. It is also possible that the switches can connect two electrodes 615 directly to one another. For an example, the switches 713b can connect the electrode 615a to a first input of the message amplifier/filter 740, and connect the electrodes 615b and 615c to one another and to a second input of the message amplifier/filter 740. Beneficially, connecting together two or more electrodes (e.g., 615b and 615c) to a same node (e.g., to the same input node of the message amplifier/filter 740) can effectively average or create a virtual vector which is between the two or more electrode locations, which enables sensing of a signal that is effectively an average of the signals detected at the two separate electrodes. This is an example of where a combination of the three electrodes 615a, 615b, and 615c includes all three of the electrodes, with the electrode 615a being separate from the other electrodes, and the electrodes 615b and 615c being electrically coupled to one another. The inclusion of three external electrodes 615 enables an ECG to be sensed at multiple vectors and/or enables selection from among the multiple vectors for conductive communication with one or more implanted LPs so that conductive communication quality can be improved or maximized.

As noted above, the conductive communication receiver 742, which is shown as including the message amplifier and/or filter 740, and the message decoder 738, is configured to receive conductive communication signals from one or more LPs (e.g., 102a and/or 102b). The message amplifier and/or filter 740 is configured to amplify and/or filter conductive communication signals received from an LP (e.g., 102a and/or 102b). The amplifier portion can be used to increase the relatively small amplitudes of such conductive communication signals. The filter portion can be a high-pass filter or a bandpass filter adapted to separate an ECG signal from conductive communication signals. The message decoder 738 can be configured to decode conductive communication signals received from an LP into a format that the controller 712 can understand. The specific type of decoding performed by the message decoder 738 depends upon the specific coding of the conductive communication signals received from an LP, e.g., on-off keying, frequency-shift keying, frequency modulation, or amplitude shift keying, but not limited thereto.

The conductive communication transmitter 732 is configured to transmit (under the controller of the controller 712) conductive communication signals to one or more IMDs implanted within a patient. One example of a conductive communication signal that may be transmitted by the external device 602, such as an external programmer or a remote monitor, is an acknowledgement (ACK) sequence of conductive communication pulses, which informs one or more LPs that the external device 602 is in proximity to the LP(s) and/or other types of IMD(s) and capable of receiving data (encoded into conducted communicate pulses) from the LP(s) and/or other types of IMD(s). The conductive communication signals can also be used to program, interrogate, and/or obtain notifications and/or other types of diagnostic information from one or more IMD(s).

The transmitter 732, in this example embodiment, is shown as including a message encoder and/or modulator 730 and an amplifier 736. The message encoder and/or modulator 730 can be configured to encode and/or modulate signals that are output from the controller 712 into a format that IMD(s) can understand. The specific type of encoding performed by the message encoder depends upon the specific type of encoding the IMD(s) can understand, e.g., on-off keying, frequency-shift keying, frequency modulation, or amplitude shift keying, but not limited thereto. The amplifier 736 is coupled to the encoder/modulator 730 to increase amplitudes of pulses included in a conductive communication signals to a level sufficient to enable one or more IMD(s) to receive conductive communication signals from the external device 602.

The controller 712 may receive ECG data and optionally displays an ECG using the display 716 and can also display information included in other data acquired from the implanted IMD(s) acquired through the encoded pulses included in conductive communication signals, such as battery voltage, sensed cardiac signal amplitude, or other system status information. The controller 712 also can accept input from a user via a user interface 718, which can include, e.g., a keyboard and/or touch-screen, but is not limited thereto. The controller 712 can also communicate over a network interface 720 to other data entry or display units, such as a handheld computer or laptop/desktop unit. The network interface 720 can be cabled or wireless and can also enable communication to a local area network or the Internet for greater connectivity. More specifically, the network interface 720 can be used to send ECG data, diagnostic data, and other types of data collected from one or more IMD(s) to a patient care network associated with a medical group and/or facility. For more specific examples, the network interface can include a Bluetooth antenna, a WiFi antenna, and/or an Ethernet connection, but is not limited thereto.

The controller 712, which can include one or more processors, and/or the like, can execute operations based on firmware stored in non-volatile memory (Flash). The non-volatile memory can also be used to store parameters or values that are to be maintained when power is removed. The controller 712 can use volatile memory or random access memory (RAM) as general storage for information such as ECG data, status information, swap memory, and other data.

The external device 602 can include or be coupled to more than three external electrodes 615. For example, the external device 602 can included or be coupled to four, five, or six external electrodes 615, but not limited thereto, wherein the greater the number of external electrodes the greater the number of potential communication vectors to test and select from.

The external electrodes (e.g., 615) of an external device (e.g., 602) described herein can be used to sense ECG signals, as well as sense conductive communication signals output by one or more IMDs. It is also possible for the external electrodes of an external device to be used to receive electrogram (EGM) signal data included in conductive communication signals output by one or more IMDs, which EGM signal data can be received by the external device (using the external electrodes) and used to reproduce one or more electrogram signals that were sensed by one or more IMDs, wherein an EGM signal can also be referred to as an intracardiac electrogram (IEGM) signal. In addition to being able to communicate with one or more IMDs via conductive communication, the external device 602 can optionally have an antenna and RF communication capabilities that enable the external device 602 to wirelessly communicate with an implantable device, such as the ICM 104, via a wireless communication protocol, examples of which were discussed above. It would also be possible for the external device 602 to also include an inductive coil that enables the external device to perform inductive communication with an IMD that has such a capability.

The external device 602 can take many physical forms, but fundamentally it should be able to establish a conductive communication vector with the patient so that it can detect one or more IMDs' conductively communicated transmissions, decipher the communication protocol utilized by the IMD(s), and upload any acquired follow-up information to a patient care network, such as the Merlin.net™ patient care network operated by Abbott Laboratories (headquartered in the Abbott Park Business Center in Lake Bluff, Illinois).

For example, where the external device 602 has or is communicatively coupled to three external electrodes 615a, 615b and 615c, which can be referred to respectively as first, second, and third external electrodes, the external device can test and select among first, second, and third subsets of the external electrodes, wherein the first subset includes the first and second external electrodes (i.e., 615a and 615b), the second subset includes the first and third external electrodes (i.e., 615a and 615c), and the third subset includes the second and third external electrodes (i.e., 615b and 615c). In accordance with certain embodiments of the present technology, which are described below, the external device 602 can identify which one of a plurality of the subsets, or more generally, which one of the plurality of possible communication vectors, is a preferred communication vector for communicating with an IMD. Further, as will be described in additional details below, where multiple IMDs are implanted within a patient, the external device can determine that different communication vectors are preferred for different IMDs. However, it is also possible that the external device may determine that a same communication vector is preferred for communicating with two or more different IMDs.

Figure 8:
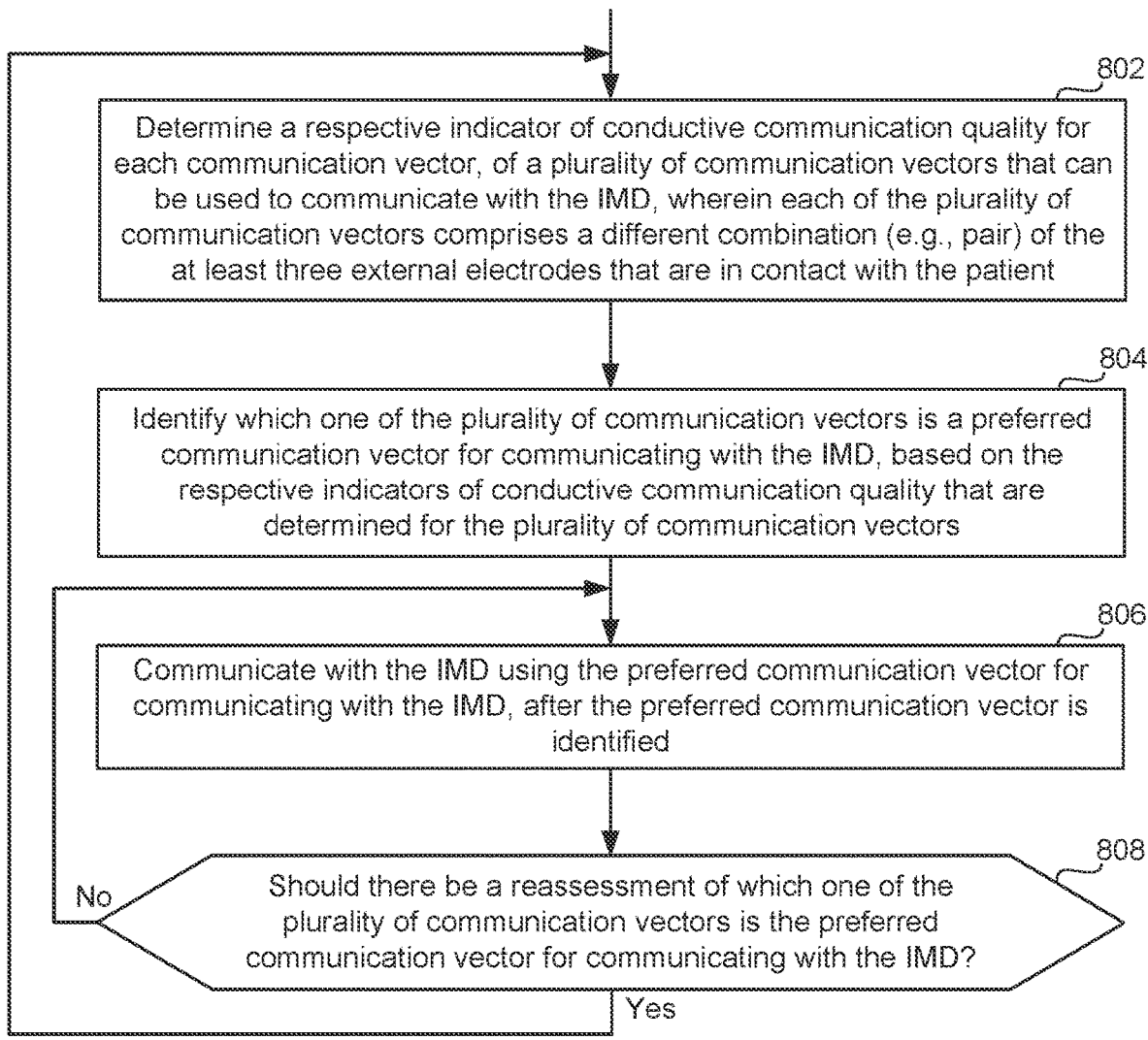
FIG. 8 is a high level flow diagram used to summarize certain methods for use by an external device that is configured to communicate with an IMD implanted within a patient using conductive communication, wherein the external device includes or is communicatively coupled to at least three external electrodes that are in contact with the patient.

The high level flow diagram of FIG. 8 will now be used to summarize certain methods for use by an external device that is configured to communicate with an IMD implanted within a patient using conductive communication, wherein the external device includes or is communicatively coupled to at least three external electrodes (e.g., external electrodes 615a, 615b and 615c) that are in contact with the patient. Referring to FIG. 8, step 802 involves determining a respective indicator of conductive communication quality for each communication vector, of a plurality of communication vectors that can be used to communicate with the IMD, wherein each of the plurality of communication vectors comprises a different combination (e.g., pair) of the at least three external electrodes that are in contact with the patient. Step 804 involves identifying which one of the plurality of communication vectors is a preferred communication vector for communicating with the IMD, based on the respective indicators of conductive communication quality that are determined for the plurality of communication vectors. Step 806 involves communicating with the IMD using the preferred communication vector for communicating with the IMD, after the preferred communication vector is identified, at step 804.

In accordance with certain embodiments, step 802 involves, for each communication vector, determining a plurality of different measures of conductive communication quality and/or surrogates thereof for the communication vector, and combining the plurality of different measures to produce the respective indicator of conductive communication quality for the communication vector. When combining the various different measures and/or surrogates thereof, the different measures and/or surrogates thereof can be equally or non-equally weighted, depending upon the specific implementation. Example measures of conductive communication quality and/or surrogates thereof that can be determined for a communication vector include, but are not limited to: a noise floor associated with the communication vector, a measure of amplitude of at least a portion of a conductive communication signal received by the external device from the IMD using the communication vector, a measure of amplitude of at least a portion of a conductive communication signal received by the IMD from the external device, a magnitude of at least a portion of a conductive communication signal received by the external device from the IMD after rectification and integration thereof, a magnitude of at least a portion of a conductive communication signal received by the IMD from the external device after rectification and integration thereof, a signal-to-noise ratio (SNR) of at least a portion of a conductive communication signal received by the external device from the IMD, a SNR of at least a portion of a conductive communication signal received by the IMD from the external device, a total energy of at least a portion of a conductive communication signal received by the external device from the IMD after rectification and integration thereof, a total energy of at least a portion of a conductive communication signal received by the IMD from the external device after rectification and integration thereof, a bit-error-rate (BER) associated with at least a portion of a conductive communication signal received by the external device from the IMD, and a BER associated with at least a portion of a conductive communication signal received by the IMD from the external device. Other variations are also possible and within the scope of the embodiments described herein.

In order for one or more measures of the quality of conductive communication signals received by an IMD from the external device to be used by the external device to identify a preferred communication vector for the external device to use for communicating with the IMD, the IMD should provide such measure(s) to the external device so that external device has such measure(s) available for use in identifying the preferred communication vector. Alternatively, in certain embodiments, the external device only considers measures of the quality of conductive communication signals received by the external device from an IMD when identifying the preferred communication vector that the external device should use for communicating with the IMD.

In accordance with certain embodiments, step 804 involves ranking the plurality of communication vectors, and identifying a highest ranked one of the plurality of communication vectors as the preferred communication vector for communicating with the IMD. Alternatively, step 804 can more simply involve identifying which one of the plurality of communication vectors has the highest indicator of conductive communication quality.

Still referring to FIG. 8, step 808 involves determining whether there should be a reassessment of which one of the plurality of communication vectors is the preferred communication vector for communicating with the IMD. Step 808 can be performed while or after communicating with the IMD using the preferred communication vector for communicating with the IMD. If the answer to the determination at step 806 is No, then flow returns to step 806. If the answer to the determination at step 806 is Yes, then flow returns to step 802, and steps 802 and 804 are performed again.

In accordance with certain embodiments, step 808 can involve determining whether an indicator of conductive communication quality associated with the preferred communication vector for communicating with the IMD has fallen below a corresponding threshold. If the answer is No then flow returns to step 806, and if the answer is Yes then flow returns to step 802. Alternatively, or additionally, step 808 can involve determining whether the external device has lost conductive communication with the IMD. Alternatively, or additionally, step 808 can involve determining whether a specified period of time has elapsed since the preferred communication vector for communicating with the IMD was most recently identified. If the answer is No then flow returns to step 806, and if the answer is Yes then flow returns to step 802.

In accordance with certain embodiments, instructions can be provided to a user of the external device to modify at least one of where or how one or more of the at least three external electrodes contact the patient, in response to determining that all of the indicators of conductive communication quality for communicating with the IMD, which are determined for the plurality of communication vectors, are below a corresponding threshold. Such instructions can be provided via a display of the external device, and/or may be auditory type instructions. Other variations are also possible.

If a plurality of IMDs that are configured to perform conductive communication are implanted within the patient, the external device can perform the steps described above with reference to FIG. 8 for each of the plurality of IMDs, such that a respective preferred communication vector is separately identified for each of the plurality of IMDs that are configured to perform conductive communication. For example, steps 802, 804, and 806 can initially be performed by the external device for a first IMD, then steps 802, 804, and 806 can be performed by the external device for a second IMD, etc. Alternatively, step 802 can be performed by the external device for each of a plurality of IMDs (e.g., a first IMD, a second IMD, etc.), then step 804 can be performed by the external device for each of a plurality of IMDs (e.g., the first IMD, the second IMD, etc.), and then step 806 can be performed by the external device for each of a plurality of IMDs (e.g., the first IMD, the second IMD, etc.). Other variations are also possible and within the scope of the embodiments described herein.

In alternative embodiments, where a plurality of IMDs that are configured to perform conductive communication are implanted within a patient, rather than an external device identifying a separate preferred communication vector for each of the plurality of IMDs, the external device can instead identify a universally preferred communication vector. In certain such embodiments, the external device can perform step 802 in FIG. 8 for each of the plurality of IMDs, such that for each of the IMDs a respective indicator of conductive communication quality is determined for each communication vector, of the plurality of communication vectors that can be used to communicate with the IMD. Step 804 can be performed collectively for the plurality of IMDs to thereby identify one preferred communication vector for communicating with the plurality of IMDs. Then, after the one preferred communication vector is identified at step 804, step 806 can involve communicating with the plurality of IMDs using the one preferred communication vector for communicating with the IMDs. The one preferred communication vector can also be referred to as a universally preferred communication vector. An advantage of identifying and using a universally preferred communication vector is that switching between different communication vectors need not be performed each time the external device wants or needs to communicate with a different one of the IMDs.

Where multiple IMDs are synchronized with one another or to a common reference, it may be viable for the external device to switch between different communication vectors each time the external device attempts to communicate with a different one of the IMDs. However, where multiple IMDs operate asynchronously, it may be difficult or impossible for an external device to attempt to communicate with different ones of the IMDs using different preferred communication vectors. Accordingly, where multiple IMDs operate asynchronously, it would likely be more viable for an external device to communicate with the multiple IMDs using a universally preferred communication vector. Such a universally preferred communication vector may not (and will likely not) provide for the highest available level of communication quality for each of the multiple IMDs, but should provide at least a minimally acceptable level of communication quality for each of the multiple IMDs. For example, there can be a minimal acceptable level of communication quality that the external device can use to successfully communicate with an IMD using conductive communication quality. The universally preferred communication vector should provide at least this minimally acceptable level of communication quality for each of the IMDs with which the external device is to conductively communicate.

For a specific example, assume an external device is to communicate with a first IMD (i.e., IMD1) and a second IMD (i.e., IMD2). Also assume that there are three different communication vectors that the external device can select, which can be referred to as Vector A, Vector B, and Vector C. Also assume for simplicity that indicators of conductive communication quality are specified as values between 0 and 10, with 0 being the worst and 10 being the best. An example of this is shown in Table 1 below.

TABLE 1

|  | Vector A | Vector B | Vector C |
|---|---|---|---|
| IMD 1 | 10 | 4 | 0 |
| IMD 2 | 6 | 8 | 0 |

Assuming that the minimally acceptable level of communication quality corresponds to a value of 5, it can be appreciated from Table 1 that the external device would select Vector A as the universally preferred communication vector, even though vector B provide for better communication quality for the IMD2. Where there are multiple different vectors that can provide the minimally acceptable level of communication quality for all the IMDs that the external device is to communicate with, the external device may identify as the universally preferred vector the specific one of the vectors that provides for the highest level of communication quality among the multiple viable vectors. In a specific embodiment, where there are multiple different vectors that can provide the minimally acceptable level of communication quality for all the IMDs that the external device is to communicate with, the external device may identify as the universally preferred vector the specific one of the vectors that provides for the highest sum or average of the values of communication quality.

Figure 9:
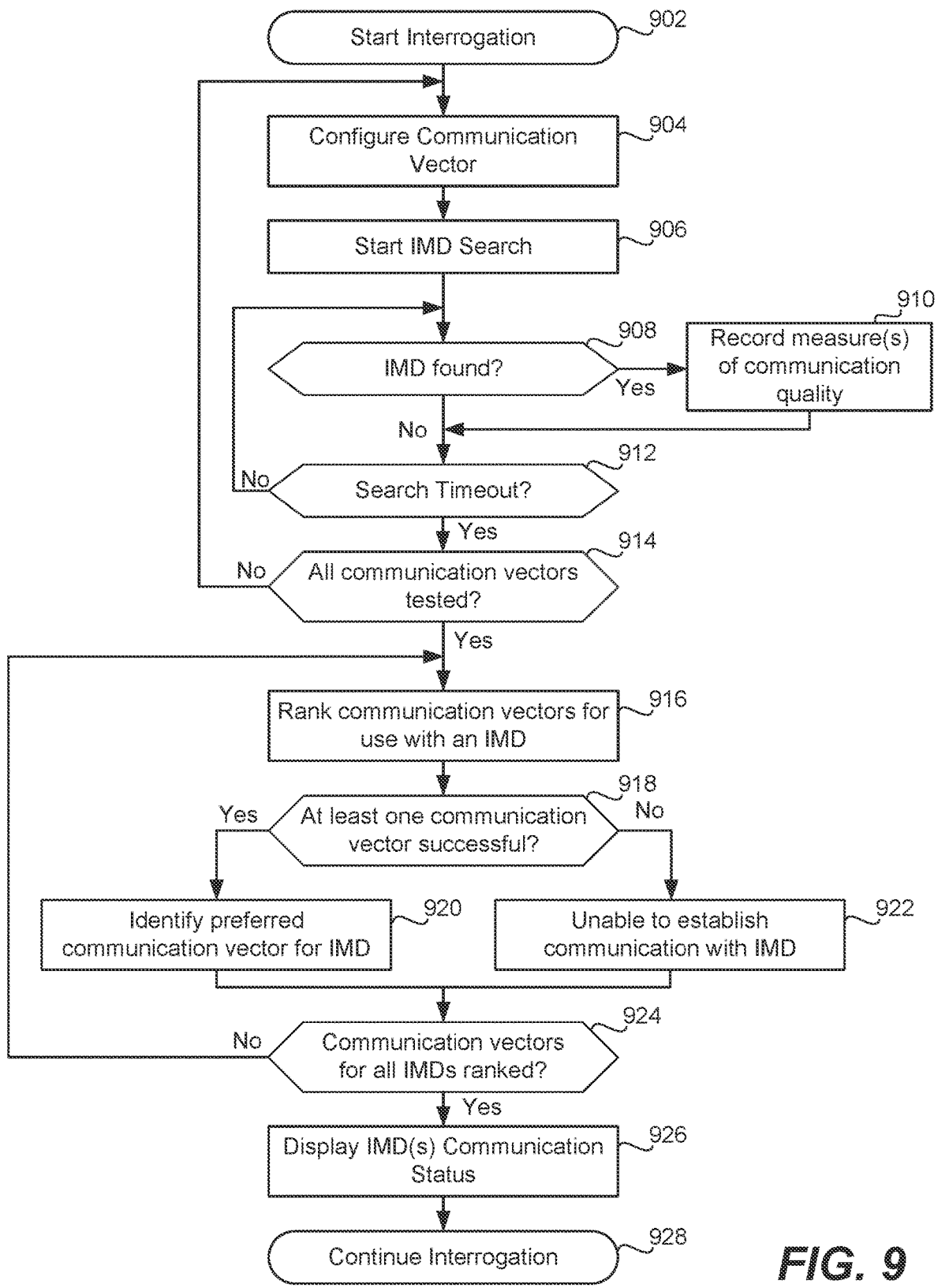
FIG. 9 is a high level flow diagram used to describe how an external device can test communication vectors as part of an interrogation of one or more IMDs.

The high level flow diagram of FIG. 9 will now be used to describe how communication vectors can be tested as part of, and more specifically at the beginning of, an interrogation of one or more IMDs by an external device. Such an interrogation can be performed, for example, by an external programmer when a patient visits a clinic for the purpose of uploading data that has been stored within the IMD(s) and/or reprogramming the IMD(s), but not limited thereto. It would also be possible that the interrogation is performed by a remote monitor that is not capable of programming the IMD(s), for the purpose of uploading data and/or notification that have been stored within the IMD(s). Other variations are also possible and within the scope of the embodiments described herein.

Referring to FIG. 9, at step 902 an interrogation of one or more IMDs by an external device is started. At step 904 the external device configures a communication vector to use for performing conductive communication with an IMD, which can involve coupling two of three or more external electrodes (e.g., 615a, 615b, and 615c) to a conductive communication receiver (e.g., 120 or 742). Step 904 can be performed by controlling switches, such as the switches 713 in FIG. 7, to control which electrodes are coupled to the conductive communication receiver of the external device.

At step 906 an IMD search is started, which can involve monitoring for sniff pulses from an IMD. At step 908 there is a determination of whether an IMD was found, which can involve determining whether sniff pulses were detected from an IMD. If the answer to the determination at step 908 is Yes (i.e., if an IMD was found), then one or more measures of communication quality can be determined and stored (e.g., in memory of the external device) at step 910. In certain embodiments, the measures of communication quality are from the perspective of the external device, meaning the measures are indicative of the quality of signals (e.g., sniff signals, but not limited thereto) received by the external device from an IMD. Alternatively, or additionally, the measures of communication quality can be from the perspective of the IMD, meaning the measures can be indicative of the quality of signals received by an IMD from the external device. Examples of measures of communication quality, or surrogates thereof, that can be measured and stored at instances of step 910 were discussed above with reference to step 802 of FIG. 8, and thus, need not be described again.

After an instance of step 910, or when the answer to the determination at step 908 is No, flow goes to step 912. At step 912 there is a determination as to whether a search for an IMD has timed out. Step 912 can be performed, for example, using a countdown or count-up timer, but is not limited thereto. If the answer to the determination at step 912 is No, then flow returns to step 908. If the answer to the determination at step 912 is Yes, then flow goes to step 914.

At step 914 there is a determination of whether all possible communication vectors have been tested. For example, if there are three total external electrodes that include first, second, and third electrodes, then there are three communication vectors that should be tested, including a first communication vector made up of the first and second electrodes, a second communication vector made up of the first and third electrodes, and a third communication vector made of the second and third electrodes. For another example, if there are four external electrodes, then there are six different communication vectors that can be tested, assuming each communication vector includes a different combination of two of the four external electrodes. For still another example, if there are five external electrodes, then there are ten different communication vectors that can be tested, assuming each communication vector includes a different combination of two of the five external electrodes. More generally, the total number (T) of different communication vectors to test can be determined using the equation $T=n!/(2! (n-2)!)$, where n is the total number of external electrode, and the exclamation mark ! represents a factorial. If the answer to the determination at step 914 is No, then flow returns to step 904 and a different one of the total number T of different communication vectors is configured at 904. When the answer to the determination at step 914 is Yes, then flow goes to step 916.

At step 916 the plurality of communication vectors that were tested are ranked from best to worst. At step 918 there is a determination of whether at least one of the communication vectors tested for an IMD was successful at conductively communicating with the IMD. In certain embodiments, step 918 can involve determining whether a sniff pulse was successfully detected from the IMD. Additionally, or alternatively, step 918 can involve determining whether at least some threshold level of communication quality was achieved. If the answer to the determination at step 918 is Yes, then flow goes to step 920. If the answer to the determination at step 918 is No, then flow goes to step 922.

At step 920 a preferred communication vector for the IMD is identified. This can involve identifying the highest ranking communication vector for the IMD, following the ranking performed at step 916. It is also possible to eliminate step 916, and at step 920 identify the communication vector that provided for the highest communication quality.

At step 922 that is a determination that conductive communication was unable to be established using any of the possible communication vectors. In certain embodiments, at or following step 922, instructions can be provided to a user of the external device to modify at least one of where or how one or more of the external electrodes contact the patient.

At step 924 there is a determination of whether communication vectors for all of the IMDs have been ranked. If the answer to the determination at step 924 is No, then flow returns to step 916 and step 916 and the following steps are repeated for another IMD. If the answer to the determination at step 924 is Yes, then flow goes to step 926. At step 926 the conductive communication status for each of the IMDs is displayed to the user of the external device. As indicated at step 928, the interrogation is continued. This can include, for example, using the preferred conductive communication vector identified at step 920 for each IMD (of one or more IMDs) to upload information from the IMD and/or to program or reprogram the IMD.

As was explained above with reference to step 808 in FIG. 8, in accordance with certain embodiments, after a preferred conductive communication vector has been identified and used for communicating with an IMD, there may be a reassessment of which one of the plurality of communication vectors is the preferred communication vector for communicating with the IMD. As was also explained above, this can involve determining whether an indicator of conductive communication quality associated with the preferred communication vector for communicating with the IMD falls below a corresponding threshold, or whether conductive communication between the external device and the IMD was lost. Additional details of when and how such a reassessment may occur, in accordance with certain embodiments of the present technology, will now be described below with reference to FIG. 10.

Figure 10:
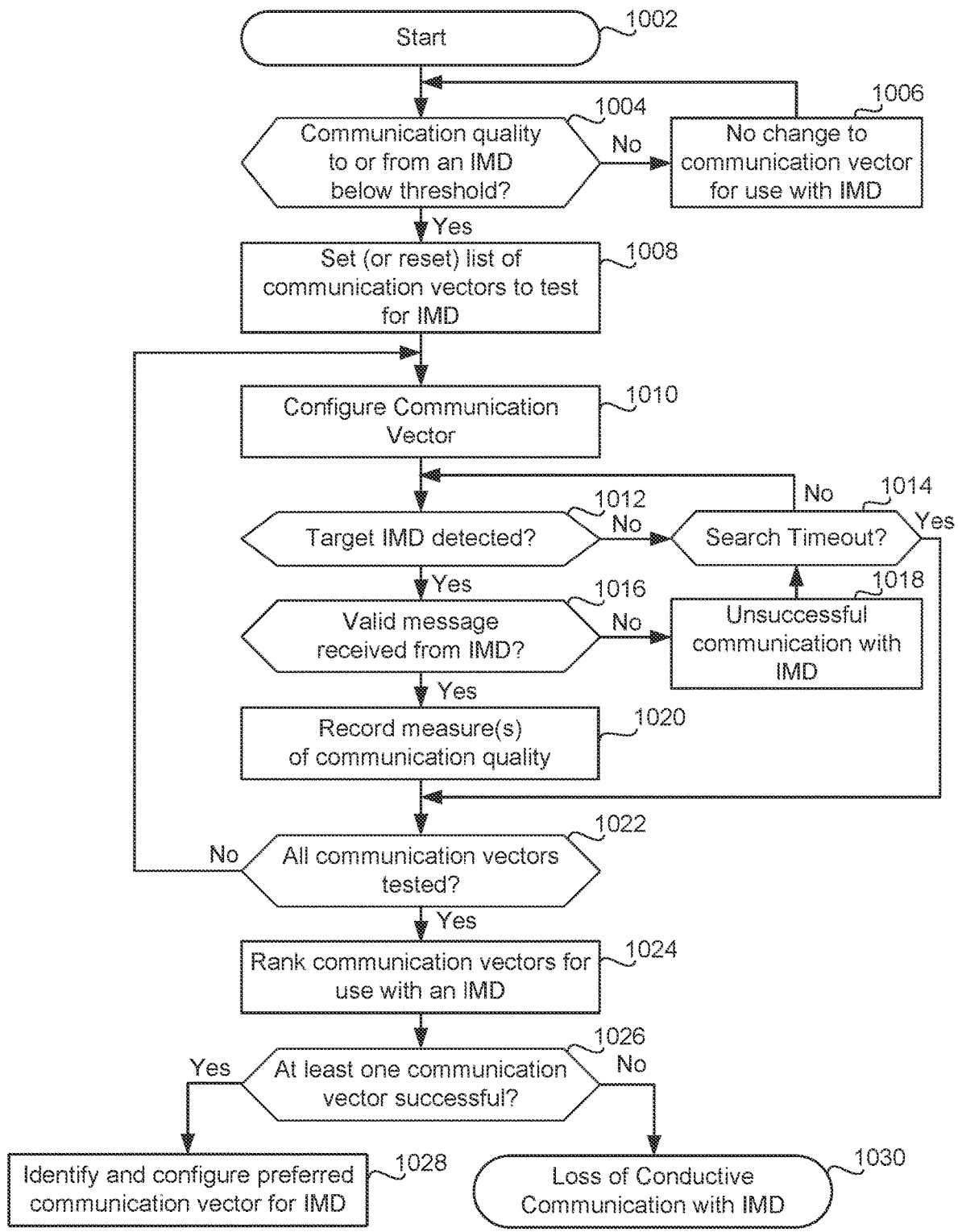
FIG. 10 is a high level flow diagram used to describe how an external device may from time to time reassess which communication vector should be used to conductively communicate with each of one or more IMDs.

Referring to FIG. 10, following a start at step 1002 there is a determination at step 1004 of whether the conductive communication quality associated with the preferred communication vector for communicating with an IMD has fallen below a corresponding threshold. If the answer to the determination at step 1004 is No, then there is no change to what is considered the preferred communication vector for communicating with the IMD, as indicated at step 1006, and then flow returns to step 1004. If the answer to the determination at step 1004 is Yes, then flow goes to step 1008. It is noted that if there is a loss of conductive communication between the external device and an IMD, the answer to the determination at step 1004 will be Yes.

At step 1008, a list of possible communication vectors to test for the IMD is set or reset. At step 1010 (which is similar to step 904 described above with reference to FIG. 9), the external device configures a communication vector to use for performing conductive communication with an IMD, which can involve coupling two of three or more external electrodes (e.g., 615a, 615b, and 615c) to a conductive communication receiver (e.g., 120 or 742). Step 1010 can be performed by controlling switches, such as the switches 713 in FIG. 7, to control which electrodes are coupled to the conductive communication receiver of the external device.

At step 1012 there is a determination of whether the IMD with which the external device is attempting to communicate (which can be referred to as the target IMD) was detected. This step can involve determining whether any communication pulses, such as sniff pulses, were detected by the external device from the target IMD. If the answer to the determination at step 1012 is No then flow goes to step 1014. At step 1014 (which is similar to step 912 described above with reference to FIG. 9) there is a determination as to whether a search for the IMD has timed out. Step 1014 can be performed, for example, using a countdown or count-up timer, but is not limited thereto. If the answer to the determination at step 1014 is No, then flow returns to step 1012. If the answer to the determination at step 1014 is Yes, then flow goes to step 1022.

Returning to step 1012, if the answer to the determination at step 1012 is Yes, then flow goes to step 1016. At step 1016 there is a determination of whether a valid message is received from the IMD. The external device can use cyclic redundancy check (CRC) or some other type of error detection and correction scheme to determine whether a message the external device receives from the IMD is a valid message or an invalid message. If there answer to the determination at step 1016 is No, then it is determined that the external device was unsuccessful at communicating with the target IMD as indicated at step 1018, and then flow goes to step 1014, which was discussed above. If the answer to step 1014 is Yes, then flow goes to step 1022.

Returning to step 1016, if the answer to the determination at step 1016 is Yes, then flow goes to step 1020. At step 1020 (which is similar to step 910 described above with reference to FIG. 9), one or more measures of communication quality are determined and stored (e.g., in memory of the external device). In certain embodiments, the measures of communication quality are from the perspective of the external device, meaning the measures are indicative of the quality of signals received by the external device from an IMD. Alternatively, or additionally, the measures of communication quality can be from the perspective of the IMD, meaning the measures can be indicative of the quality of signals received by an IMD from the external device. Examples of measures of communication quality, or surrogates thereof, that can be measured and stored at instances of step 1020 were discussed above with reference to step 802 of FIG. 8, and thus, need not be described again.

At step 1022 (which is similar to step 914 described above with reference to FIG. 9), there is a determination of whether all possible communication vectors have been tested. For example, if there are three total external electrodes that include first, second, and third electrodes, then there are three communication vectors that should be tested, including a first communication vector made up of the first and second electrodes, a second communication vector made up of the first and third electrodes, and a third communication vector made of the second and third electrodes. More generally, the total number (T) of different communication vectors to test can be determined using the equation $T=n!/(2!\,(n-2)!)$, where n is the total number of external electrode, and the exclamation mark ! represents a factorial. If the answer to the determination at step 1022 is No, then flow returns to step 1010 and a different one of the total number T of different communication vectors is configured at 1010. When the answer to the determination at step 1022 is Yes, then flow goes to step 1024.

At step 1024 (which is similar to step 916 described above with reference to FIG. 9) the plurality of communication vectors that were tested are ranked from best to worst. At step 1026 there is a determination of whether at least one of the communication vectors tested for an IMD was successful at conductively communicating with the IMD. In certain embodiments, step 1026 can involve determining whether a sniff pulse was successfully detected from the IMD. Additionally, or alternatively, step 1026 can involve determining whether at least some threshold level of communication quality was achieved. If the answer to the determination at step 1026 is Yes, then flow goes to step 1028. If the answer to the determination at step 1026 is No, then flow goes to step 1030.

At step 1028 a preferred communication vector for the IMD is identified. This can involve identifying the highest ranking communication vector for the IMD, following the ranking performed at step 1024. It is also possible to eliminate step 1024, and at step 1028 identify the communication vector that provided for the best communication quality. At step 1030 there is a determination that conductive communication was unable to be reestablished using any of the possible communication vectors, and thus, the conductive communication with the target IMD was lost (or continues to be lost). In certain embodiments, at or following step 1030, instructions can be provided to a user of the external device to modify at least one of where or how one or more of the external electrodes contact the patient.

Figure 11:
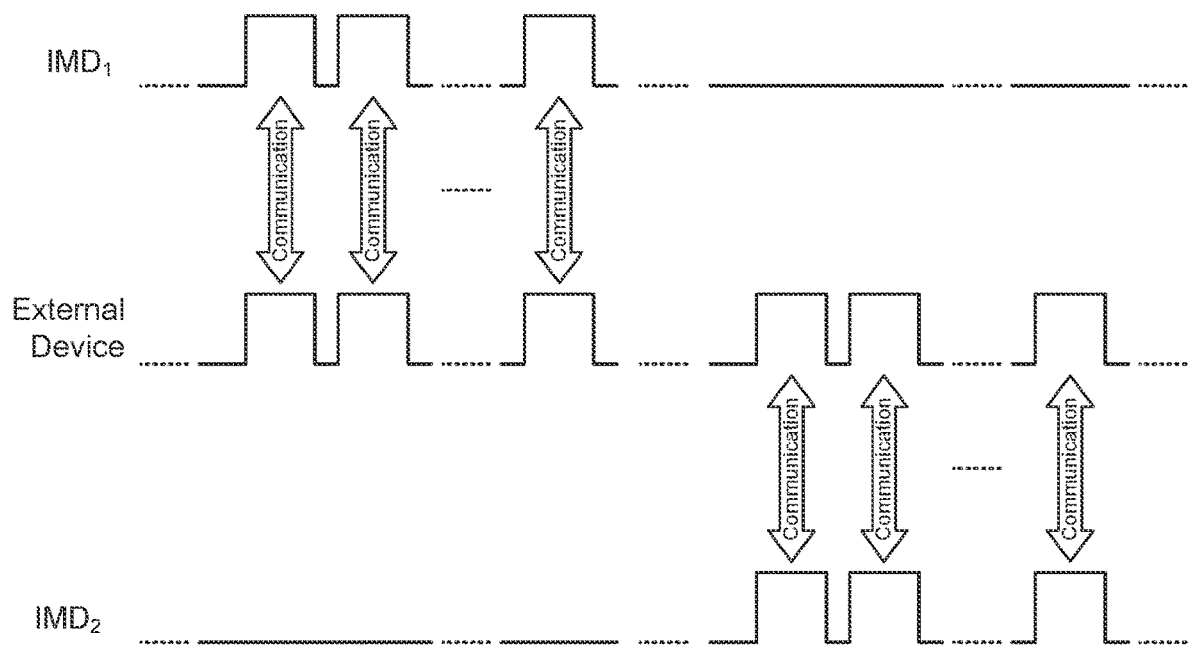
FIG. 11 includes a timing diagram that shows how an external device can conductively communicate with a first IMD during a first period of time using a preferred communication vector identified by the external device for communicating with the first IMD, and can conductively communicate with a second IMD during a second period of time using a preferred communication vector identified by the external device for communicating with the second IMD.

FIG. 11 includes a timing diagram that shows how an external device can conductively communicate with a first IMD ($IMD_1$) during a first period of time using a preferred communication vector identified by the external device for communicating with the first IMD. FIG. 11 also shows that the external device can thereafter conductively communicate with a second IMD ($IMD_2$) during a second period of time using a preferred communication vector identified by the external device for communicating with the second IMD. Such preferred communication vectors can be identified using one of the embodiments described above, e.g., with reference to FIG. 8 and FIG. 9. Depending upon the positions of the IMDs relative to the external electrodes, the preferred conductive communication vector for communicating with the second IMD can be different (or potentially the same) as the preferred conductive communication vector for communicating with the first IMD.

Figure 12:
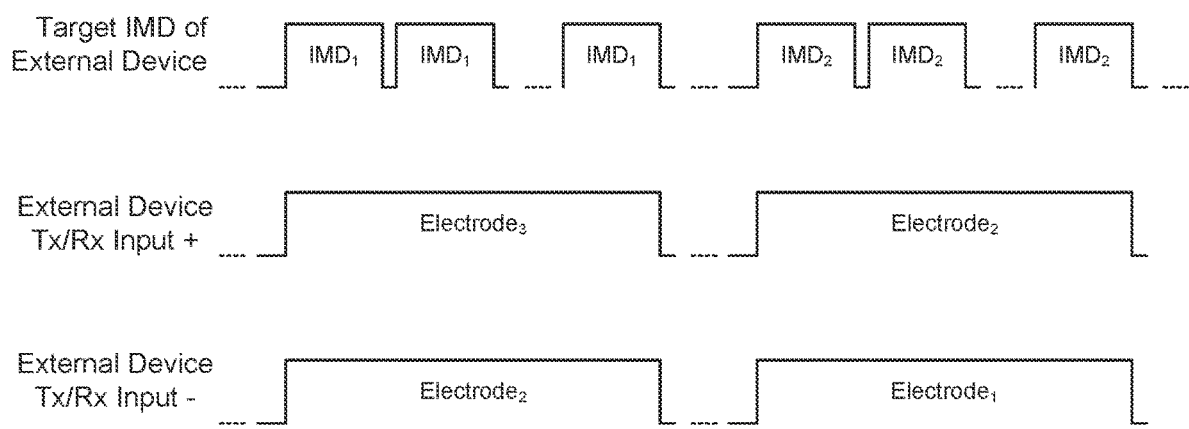
FIG. 12 includes a timing diagram that shows that during a first period of time an external device communicates with a first IMD using a first communication vector, and during a second period of time communicates with a second IMD using a second communication vector.

FIG. 12 includes a timing diagram that shows that during a first period of time, during which the target IMD is a first IMD ($IMD_1$), the external device communicates with the first IMD using a communication vector that includes a third electrode ($Electrode_3$) and a second electrode ($Electrode_2$). FIG. 12 also shows that during a second period of time, during which the target IMD is a second IMD ($IMD_2$), the external device communicates with the second IMD using a communication vector that includes the second electrode ($Electrode_2$) and a first electrode (Electrodes). For this example, it is assumed that the conductive communication transceiver, which includes a conductive communication receiver, has differential inputs, including a positive (+) input and a negative (−) input. FIG. 12 also shows that communication with each target device (e.g., $IMD_1$ or $IMD_2$) can include one or more communication frames/packets/bursts.

In accordance with certain embodiments of the present technology, an external device can perform the steps described below with reference to FIG. 13 to identify a preferred communication vector, and receive a notification sequence, or more generally a conductive communication signal, from an implanted IMD (e.g., an LP) using the identified preferred communication vector. For the embodiment described below with reference to FIG. 13, it is assumed that three electrodes are in contact with the patient, wherein the three electrodes can be referred to as first, second, and third electrodes. Where a communication vector is being used to receive a conductive communication signal, the communication vector can be referred to as a sensing vector.

Figure 13:
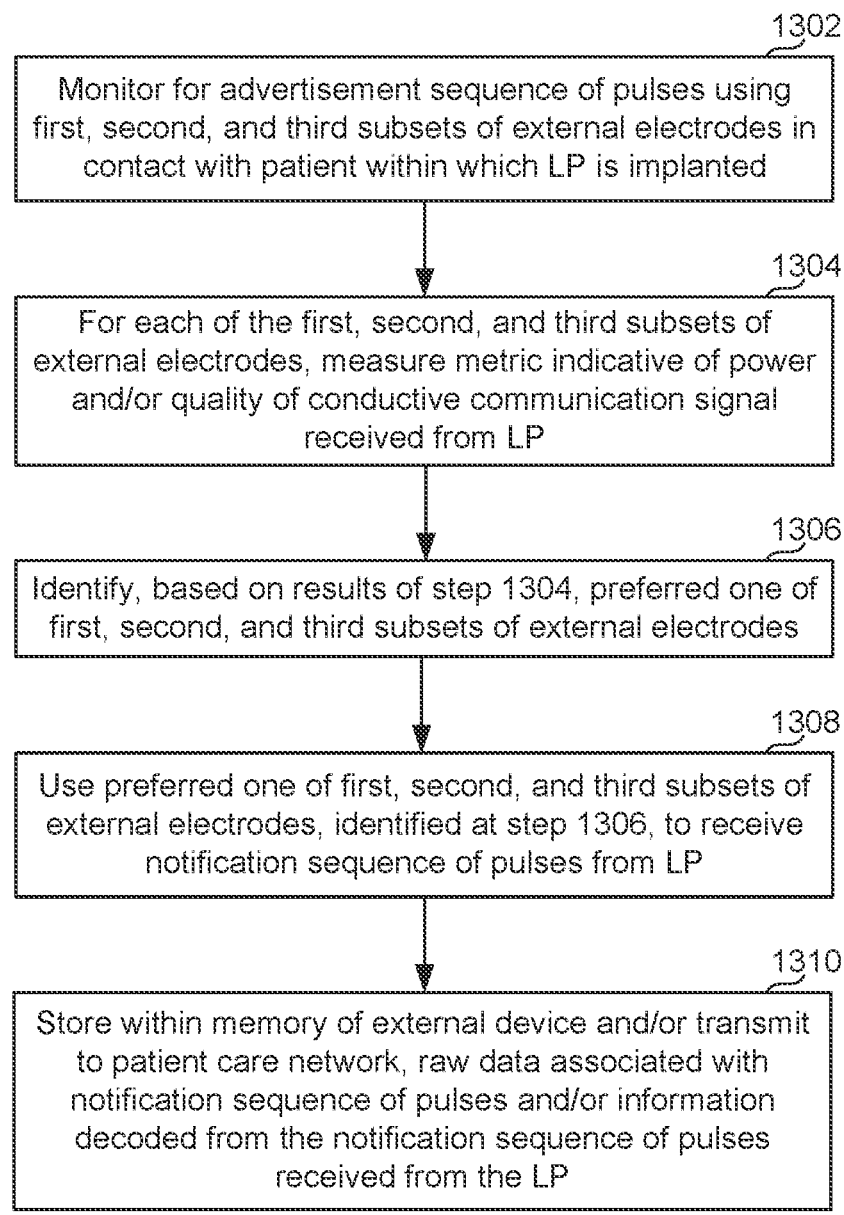
FIG. 13 is a high level flow diagram that is used to summarize a method in which an external device can select a preferred communication vector, from among three or more external electrodes, for receiving conductive communication signals from an implanted IMD.

FIG. 13 is a high level flow diagram that is used to summarize a specific method in which an external device can select a preferred communication vector (e.g., sensing vector), from among three or more external electrodes, for receiving conductive communication signals from an implanted IMD. Step 1302 involves the external device monitoring for the advertisement sequence of pulses using first, second, and third subsets of the external electrodes, the first subset including the first and second external electrodes, the second subset including the first and third external electrodes, and the third subset including the second and third external electrodes. For example, at step 1302 the external device monitors for conductive communication pulses (output by an implanted LP, or other type of IMD) using a plurality of different communication vectors. The advertisement sequence of pulses can also be referred to as a sniff sequence of pulses, or more succinctly as a sniff, as was noted above.

At step 1304, the external device measures for each subset of the external electrodes, of the first, second, and third subsets, a respective metric indicative of power and/or quality of a communication signal received from the LP using the subset of electrodes. More generally, at step 1302 the external device determines a metric of power and/or quality for each of the plurality of different communication vectors.

At step 1306, the external device identifies, based on the results of step 1304, a preferred one of the first, second, and third subsets of the external electrodes. More generally, at step 1306 the external device selects a preferred communication vector, based on the results of step 1304.

At step 1308, the external device uses the preferred one of the first, second, and third subsets of the external electrodes, which was identified at step 1306, to receive the notification sequence of pulses from the LP. More generally, at step 1308 the external device uses the identified preferred communication vector to receive one or more conductive communication signals from an LP.

At step 1310, the external device stores within memory of the external device and/or transmits to a patient care network, raw data associated with the notification sequence of pulses and/or information decoded from the notification sequence of pulses received from the LP using the preferred one of the first, second, and third subsets of the external electrodes. More generally, at step 1310 the external device stores and/or forwards data it obtained from one or more conductive communication signals received from an implanted LP using the identified preferred communication vector.

In accordance with certain alternative embodiments, rather than an external device identifying a preferred communication vector for communicating with each of one or more IMDs, and then using the preferred communication vector(s) for communicating with the IMD(s), the external device can from time to time change what communication vector is uses for communicating with IMD(s), e.g., in a round robin manner, using even or odd skipping, etc. This may result in the external device from time to time being unable to communicate with one or more IMDs. However, over time, as the communication vectors that are used for performing conductive communication are changed, the external device should be able to successfully communicate with the IMD(s).

It is to be understood that the subject matter described herein is not limited in its application to the details of construction and the arrangement of components set forth in the description herein or illustrated in the drawings hereof. The subject matter described herein is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Further, it is noted that the term "based on" as used herein, unless stated otherwise, should be interpreted as meaning based at least in part on, meaning there can be one or more additional factors upon which a decision or the like is made. For example, if a decision is based on the results of a comparison, that decision can also be based on one or more other factors in addition to being based on results of the comparison.

Embodiments have been described above with the aid of functional building blocks illustrating the performance of specified functions and relationships thereof. The boundaries of these functional building blocks have often been defined herein for the convenience of the description. Alternate boundaries can be defined so long as the specified functions and relationships thereof are appropriately performed. Any such alternate boundaries are thus within the scope and spirit of the claimed invention. For example, it would be possible to combine or separate some of the steps shown in the various flow diagrams. It would also be possible to just perform a subset of the steps shown in the various flow diagrams. For another example, it is possible to change the boundaries of some of the block diagrams.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the embodiments without departing from its scope. While the dimensions, types of materials and coatings described herein are intended to define the parameters of the embodiments of the present technology, they are by no means limiting and are exemplary embodiments. Many other embodiments will be apparent to those of skill in the art upon reviewing the above description. The scope of the embodiments of the present technology should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means—plus-function format and are not intended to be interpreted based on 35 U.S.C. § 112(f), unless and until such claim limitations expressly use the phrase "means for" followed by a statement of function void of further structure.

What is claimed is:

1. A method for use by an external device that is configured to communicate with each of a plurality of implantable medical devices (IMDs) implanted within a patient using conductive communication, wherein the external device includes or is communicatively coupled to at least three external electrodes that are in contact with the patient, the method comprising:

determining for each IMD of the plurality of IMDs a respective indicator of conductive communication quality for each communication vector of a plurality of communication vectors that can be used by the external device to communicate with the IMD, wherein each of the plurality of communication vectors comprises a different combination of the at least three external electrodes that are in contact with the patient;

identifying which one of the plurality of communication vectors is a universally preferred communication vector that provides for at least a minimally acceptable level of communication quality between the external device and each of the plurality of IMDs, wherein the identifying is based on the respective indicators of conductive communication quality that are determined for each IMD of the plurality of IMDs using each of the plurality of communication vectors; and communicating with each of the plurality of IMDs using the universally preferred communication vector, after the universally preferred communication vector is identified.

2. The method of claim 1, further comprising:
while or after communicating with the plurality of IMDs using the universally preferred communication vector for communicating with the plurality of IMDs, determining whether there should be a reassessment of which one of the plurality of communication vectors is the universally preferred communication vector for communicating with the plurality of IMDs; and
in response to determining that there should be the reassessment, repeating the determining and the identifying steps.

3. The method of claim 2, wherein the determining that there should be the reassessment occurs in response to at least one of the following:
detecting the indicator of conductive communication quality associated with the universally preferred communication vector for communicating with the plurality of IMDs falling below a corresponding threshold for at least one of the plurality of IMDs;
detecting a loss of conductive communication with at least one of the plurality of IMDs; or
detecting a specified period of time elapsing since the universally preferred communication vector for communicating with the plurality of IMDs was most recently identified.

4. The method of claim 1, further comprising:
determining that at least one of the indicators of conductive communication quality for communicating with at least one of the plurality of IMDs has fallen below a corresponding threshold; and
providing instructions to a user of the external device to modify at least one of where or how one or more of the at least three external electrodes contact the patient, in response to the determining that the at least one of the indicators of conductive communication quality for communicating with the at least one of the plurality of IMDs has fallen below the corresponding threshold.

5. The method of claim 1, wherein:
the external device comprises an external programmer; and
at least one of the plurality of IMDs comprises a leadless cardiac pacemaker, an insertable cardiac monitor, or a non-vascular implantable cardioverter defibrillator.

6. The method of claim 1, wherein the determining the respective indicator of conductive communication quality for each communication vector, of the plurality of communication vectors that can be used to communicate with each of the plurality of IMDs, includes for each communication vector:
determining a plurality of different measures of conductive communication quality and/or surrogates thereof for the communication vector; and
combining the plurality of different measures of conductive communication quality and/or the surrogates thereof to produce the respective indicator of conductive communication quality for the communication vector.

7. The method of claim 6, wherein the plurality of different measures of conductive communication signal quality and/or the surrogates thereof that are determined for each communication vector, of the plurality of communication vectors that can be used to communicate with each of the plurality of IMDs, are indicative of at least two of the following:
a noise floor associated with the communication vector;
a measure of amplitude of at least a portion of a conductive communication signal received by the external device from one of the plurality of IMDs using the communication vector;
a measure of amplitude of at least a portion of a conductive communication signal received by one of the plurality of IMDs from the external device;
a magnitude of at least a portion of a conductive communication signal received by the external device from one of the plurality of IMDs after rectification and integration thereof;
a magnitude of at least a portion of a conductive communication signal received by one of the plurality of IMDs from the external device after rectification and integration thereof;
a signal-to-noise ratio (SNR) of at least a portion of a conductive communication signal received by the external device from one of the plurality of IMDs;
a SNR of at least a portion of a conductive communication signal received by one of the plurality of IMDs from the external device;
a total energy of at least a portion of a conductive communication signal received by the external device from one of the plurality of IMDs, after rectification and integration thereof;
a total energy of at least a portion of a conductive communication signal received by one of the plurality of IMDs from the external device, after rectification and integration thereof;
a bit-error-rate (BER) associated with at least a portion of a conductive communication signal received by the external device from one of the plurality of IMDs; and
a BER associated with at least a portion of a conductive communication signal received by one of the plurality of IMDs from the external device.

8. The method of claim 1, wherein when there are multiple different communication vectors that provide at least the minimally acceptable level of communication quality for all the plurality of IMDs, the identifying which one of the plurality of communication vectors is the universally preferred communication vector for communicating with the plurality of IMDs comprises identifying which one of the plurality of communication vectors has a highest sum or average of the indicators of conductive communication quality.

9. The method of claim 1, further comprising:
determining that only one of the plurality of communication vectors, which can be used to communicate with each of the plurality of IMDs, provides for at least the minimally acceptable level of communication quality between the external device and each of the plurality of IMDs; and
wherein the identifying step includes identifying, as the universally preferred communication vector for communicating with each of the plurality of IMDs, the only one of the plurality of communication vectors that provides for at least the minimally acceptable level of communication quality between the external device and each of the plurality of IMDs.

10. The method of claim 1, further comprising:
determining for each of the IMDs a respective indicator of conductive communication quality for each communication vector of the plurality of communication vectors;

determining that multiple different communication vectors of the plurality of communication vectors, which can be used to communicate with each of the plurality of IMDs, provides for at least the minimally acceptable level of communication quality between the external device and each of the plurality of IMDs; and wherein the identifying step includes identifying, as the ene universally preferred communication vector for communicating with the plurality of IMDs, the one of the plurality of communication vectors that provides for a highest sum or average of the indicators of communication quality between the external device and the plurality of IMDs.

11. The method of claim 10, wherein the identifying the one of the plurality of communication vectors that provides for the highest level sum or average of the indicators of communication quality between the external device and the plurality of IMDs, comprises identifying which one of the plurality of communication vectors provides for the highest sum of the indicators of communication quality between the external device and the plurality of IMDs.

12. The method of claim 10, wherein the identifying the one of the plurality of communication vectors that provides for the highest sum or average of the indicators of communication quality between the external device and the plurality of IMDs, comprises identifying which one of the plurality of communication vectors provides for the highest average of the indicators of communication quality between the external device and the plurality of IMDs.

13. An external device configured to communicate with each of a plurality of implantable medical device (IMD) implanted within a patient using conductive communication, the external device comprising:
 a conductive communication receiver;
 switches between the conductive communication receiver and at least three external electrodes that are configured to be placed in contact with the patient; and
 a controller configured to
  control the switches to thereby control which communication vector, of a plurality of communication vectors that can be used to communicate with each of the plurality of IMDs, is coupled to the conductive communication receiver, wherein each of the plurality of communication vectors comprises a different combination of the at least three external electrodes;
  determine for each IMD of the plurality of IMDs a respective indicator of conductive communication quality for each communication vector, of the plurality of communication vectors that can be used by the external device to communicate with the IMD;
  identify which one of the plurality of communication vectors is a universally preferred communication vector that provides for at least a minimally acceptable level of communication quality between the external device and each of the plurality of IMDs, based on the respective indicators of conductive communication quality that are determined for each IMD of the plurality of IMDs using each of the plurality of communication vectors; and
  use the universally preferred communication vector to communicate with each of the plurality of IMDs, after the universally preferred communication vector is identified.

14. The external device of claim 13, wherein the controller is also configured to determine when there should be a reassessment of which one of the plurality of communication vectors is the universally preferred communication vector for communicating with the plurality of IMDs.

15. The external device of claim 14, wherein the controller is configured to determine that there should be the reassessment in response to at least one of the following:
 the controller detecting the indicator of conductive communication quality associated with the universally preferred communication vector for communicating with the plurality of IMDs falling below a corresponding threshold for at least one of the IMDs;
 the controller detecting a loss of conductive communication with at least one of the plurality of IMDs; or
 the controller detecting a specified period of time elapsing since the universally preferred communication vector for communicating with the plurality of IMDs was most recently identified.

16. The external device of claim 13, wherein in order to determine the respective indicator of conductive communication quality for each communication vector, of the plurality of communication vectors that can be used to communicate with each IMD of the plurality of IMDs, the controller is configured to:
 determine, for each communication vector, a plurality of different measures of conductive communication quality and/or surrogates thereof for the communication vector; and
 combine the plurality of different measures of conductive communication quality and/or the surrogates thereof to produce the respective indicator of conductive communication quality for the communication vector.

17. The external device of claim 16, wherein the plurality of different measures of conductive communication signal quality and/or the surrogates thereof that are determined for each communication vector, of the plurality of communication vectors that can be used to communicate with each IMD if the plurality of IMDs, are indicative of at least two of the following:
 a noise floor associated with the communication vector;
 a measure of amplitude of at least a portion of a conductive communication signal received by the external device from one of the plurality of IMDs using the communication vector;
 a measure of amplitude of at least a portion of a conductive communication signal received by one of the plurality of IMDs from the external device;
 a magnitude of at least a portion of a conductive communication signal received by the external device from one of the plurality of IMDs after rectification and integration thereof;
 a magnitude of at least a portion of a conductive communication signal received by one of the plurality of IMDs from the external device after rectification and integration thereof;
 a signal-to-noise ratio (SNR) of at least a portion of a conductive communication signal received by the external device from one of the plurality of IMDs;
 a SNR of at least a portion of a conductive communication signal received by one of the plurality of IMDs from the external device;
 a total energy of at least a portion of a conductive communication signal received by the external device from one of the plurality of IMDs, after rectification and integration thereof;
 a total energy of at least a portion of a conductive communication signal received by one of the plurality of IMDs from the external device, after rectification and integration thereof;

a bit-error-rate (BER) associated with at least a portion of a conductive communication signal received by the external device from one of the plurality of IMDs; and a BER associated with at least a portion of a conductive communication signal received by one of the plurality of IMDs from the external device.

18. The external device of claim 13, wherein in order to identify which one of the plurality of communication vectors is the universally preferred communication vector for communicating with each of the plurality of IMDs when there are multiple different communication vectors that provide at least the minimally acceptable level of communication quality for all the plurality of IMDs, the controller is configured to identify which one of the plurality of communication vectors has a highest sum or average indicator of conductive communication quality.

19. A method for use by an external device that is configured to communicate with each implantable medical device (IMD), of a plurality of IMDs implanted within a patient, using conductive communication, wherein the external device includes or is communicatively coupled to at least three external electrodes that are in contact with the patient, the method comprising:

for each IMD, of the plurality of IMDs, determining a respective indicator of conductive communication quality for each communication vector, of a plurality of communication vectors that can be used to communicate with the IMD, wherein each of the plurality of communication vectors comprises a different combination of the at least three external electrodes that are in contact with the patient;

identifying, based on the respective indicators of conductive communication quality that are determined, a universally preferred communication vector for communicating with each the plurality of IMDs;

communicating with each of the plurality of IMDs using the one universally preferred communication vector that is identified; and determining that there should be a reassessment of which one of the plurality of communication vectors is the universally preferred communication vector for communicating with the plurality of IMDs, and in response thereto, repeating the determining and the identifying steps to thereby identify an updated universally preferred communication vector for communicating with the plurality of IMDs.

20. The method of claim 19, wherein the determining that there should be a reassessment of which one of the plurality of communication vectors is the universally preferred communication vector for communicating with each of the plurality of IMDs occurs in response to at least one of the following:

for at least one of the plurality of IMDs, detecting the indicator of conductive communication quality associated with the ene universally preferred communication vector for communicating with at least one of the plurality of IMDs falling below a corresponding threshold; or detecting a loss of conductive communication with at least one of the plurality of IMDs.

\* \* \* \* \*